United States Patent
Gellissen et al.

(10) Patent No.: US 7,045,611 B2
(45) Date of Patent: May 16, 2006

(54) NUCLEIC ACID MOLECULE, COMPRISING A NUCLEIC ACID CODING FOR A POLYPEPTIDE WITH CHORISMATE MUTASE ACTIVITY

(75) Inventors: Gerd Gellissen, Wülfrath (DE); Gerhard Braus, Goettingen (DE); Ralph Pries, Goettingen (DE); Sven Krappmann, Goettingen (DE); Alexander W. Strasser, Dusseldorf (DE)

(73) Assignee: Rhein Biotech Gesellschaft für neue Biotechnologische Prozesse und Produkte mbH, Düsseldorf (DE)

( * ) Notice: Subject to any disclaimer, the term of this patent is extended or adjusted under 35 U.S.C. 154(b) by 353 days.

(21) Appl. No.: 10/042,059

(22) Filed: Oct. 25, 2001

(65) Prior Publication Data

US 2002/0197704 A1    Dec. 26, 2002

Related U.S. Application Data

(63) Continuation of application No. PCT/EP00/03844, filed on Apr. 27, 2000.

(30) Foreign Application Priority Data

Apr. 27, 1999    (DE) ............................... 199 19 124

(51) Int. Cl.
 *C12P 21/06*    (2006.01)
 *C07H 21/04*    (2006.01)
(52) U.S. Cl. ................ 536/23.1; 536/23.11; 536/23.2; 536/23.4; 536/23.74; 435/41; 435/69.1; 435/69.7; 435/71.1; 435/71.2; 435/243
(58) Field of Classification Search ................ 435/41, 435/69.1, 69.8, 69.9, 71.1, 89, 91.1, 440, 435/471, 476, 479, 481, 483, 243, 252.3, 435/254.1, 254.11, 255.1, 255.6, 320.1, 69.7; 536/22.1, 23.1, 23.2, 23.4, 23.74, 24.1, 24.11
See application file for complete search history.

(56) References Cited

OTHER PUBLICATIONS

MacBeath et al.. A small, thermostable, and multifunctional chorismate mutase from the archeon *Methanococcus jannachii*. Jun. 1998. Biochemistry 37: 10062-10073.*
Eberhard et al. Cytosolic and plastidic chorismate mutase isozymes from *Arabidopsis thaliana*: molecular characterization and enzymatis properties. Nov. 1996. The Plant Journal 10: 815-821.*
Gray et al. Monofunctional chorismate mutase from *Bacillus subtilis*: purification of the protein, molecular cloning of the gene, and overexpression of the gene product in *Escherichia coli*. 1990. Biochemistry 29: 376-383.*
Everett et al. Pendred syndrome is caused by mutations in a putative sulphate transporter gene (PDS). Nature Genetics 17: 411-422, 1997.*
Scott et al. The pendred syndrome gene encodes a chloride-iodide trasnport protein. Nature Genetics 21: 440-443, 1999.*
Agaphonov, M. O., et al., 1994, Yeast 10, 509-513.
Arnold, C. E., et al., 1998, Biotechnol. Bioeng. 59, 286-293.
Austin, S., et al., 1981, Cell 25, 729-736.
Birnboim H. C., et al., 1979, Nucl. Acids Res. 7, 1513-1523.
Boeke, J. D., et al., 1984, Mol. Gen. Genet. 197, 345-346.
Bradford, M. M. 1976, Anal. Biochem. 72, 248-254.
Braus, G. H. 1991, Microbiol. Rev. 55. 349-370.
Buckholtz, R. G., et al., 1991, Biotechnology 9, 1067-1072.
Dobson, M. J., et al., 1982, Nucl. Acids Res. 10, 2625-2637.

(Continued)

Primary Examiner—David Guzo
Assistant Examiner—David Lambertson

(57) ABSTRACT

The invention relates to a nucleic acid molecule, comprising a nucleic acid which codes for a polypeptide with chorismate mutase activity and derivatives thereof, whereby the derivatives have at least 10% of the chorismate mutase activity of the chorismate mutase, according to the identification number of the SEQ ID NO:2. The invention further relates to vectors containing nucleic acid molecules, to host cells comprising nucleic acid molecules and their use in methods for producing polypetides with chorismate mutase activity. The invention also relates to the polypeptides with chorismate mutase activity and antibodies which specifically recognize the same. In addition, the invention relates to methods for producing auxotrophic yeast strains using the nucleic acid molecules and to the preparation of the yeast strains. The invention also relates to the use of yeast strains together with the inventive vectors in methods for the recombinant expression of heterologous genes which allow the transformants to be easily selected by functional complementation.

15 Claims, 6 Drawing Sheets

OTHER PUBLICATIONS

Dohmen, R. J., et al., 1990, Gene 95, 111-121.
Gellissen, G. et al., 1997, Gene 190, 87-97.
Gilbert, S. C., et al., 1994, Yeast 10, 1569-1580.
Godecke, S., et al., 1994, Gene 139, 35-42.
Güldener, U., et al., 1996, Nucl. Acids Res. 24, 2519-2524.
Hoffman, C. S., et al., 1987, Gene 57, 267-272.
Inoue, H., et al., 1990, Gene 96, 23-28.
Ito, H., et al., 1983, J. Bacteriol. 153, 163-168.
Janowicz, Z. A., et al., 1985, Nucl. Acids Res. 13, 3043-3062.
Jensen, R. A., et al., 1975, J. Mol. Evol. 4, 249-259.
Kradolfer, P., et al., 1977, FEMS Microbiol. Lett. 2, 211-216.
Ledeboer, A. M., et al., 1985, Nucl. Acids Res. 13, 3063-3082.
Lepetic, A., et al., 1996, Clin. Infect. Dis. 23, 276.
Lorence, J. H., et al., 1967 Biochemistry 6, 1541-1552.
Muller, S., et al., 1998, Yeast, 14, 1267-1283.
Rave, N., et al., 1979, Nucl. Acids Res. 6, 3559-3567.
Saiki, R. K., et al., 1985, Science 230, 1350-1354.
Schmidheini, T., et al., 1989, J. Bacteriol. 171, 1245-1253.
Schneider, B. L., et al., 1996, Yeast 12, 129-134.
Sikorski, R. S., et al., 1989 Genetics 122, 19-27.
Southern, E. M. 1975, J. Mol. Biol. 98, 503-517.
Steiner, S., et al., 1994, Mol. Gen. Genet. 242, 263-271.
Van der Klei, I. J., et al., 1991, Arch. Microbiol. 156, 15-23.
Verduyn, C., et al., 1992, Yeast 8, 501-517.
Weidemann, W., et al.,. (1989), FEBS Left. 257, 31-34.
Weydemann, U., et al., 1995, Appl. Microbiol. Biotechnol. 44, 377-385.
Woodcock, D. M. 1989 Nucl. Acids Res. 17, 3469-3478.

* cited by examiner

```
cccggcccaatgccagcaatatggagacgtttaggcagaataggcgttccatacttctcacgctgcttgttgcca ccggaatatacaccgcattgcagtttgcacacatcatactatatgacgattacattggcggaacgtatcgcgagt cgctcacgagacgcattagaatgacagagaaatcgcgaaacgacctatatagacgcacgtgaaaactacgggttg gaggcagcaaggaggagcgaatccagcggttttgtggttcagacatctttcgtggcttttaggcgaggataagg aacttgaggagcgtttttttttcctgtttagtttttgtaagtATGGACTTTATGAAGCCAGAAACAGTGCTGGA
                                           M  D  F  M  K  P  E  T  V  L  D
CCTTGGCAACATTAGAGATGCCTTGGTCCGGATGGAGGATACGATCATCTTCAACTTTATCGAGCGGTCGCAGTT
 L  G  N  I  R  D  A  L  V  R  M  E  D  T  I  I  F  N  F  I  E  R  S  Q  F
CTATGCGTCGCCCTCGGTATACAAAGTCAACCAGTTCCCTATTCCCAACTTCGACGGCTCGTTCTTGGACTGGCT
 Y  A  S  P  S  V  Y  K  V  N  Q  F  P  I  P  N  F  D  G  S  F  L  D  W  L
GTTGTCGCAGCACGAGCGAATCCATTCGCAGGTGAGGAGATACGACGCGCCAGACGAGGTGCCTTTTTTCCCCAA
 L  S  Q  H  E  R  I  H  S  Q  V  R  R  Y  D  A  P  D  E  V  P  F  F  P  N
CGTGCTGGAAAAAACGTTTCTGCCCAAGATCAACTACCCATCGGTGCTAGCCTCCTACGCGGATGAAATCAACGT
 V  L  E  K  T  F  L  P  K  I  N  Y  P  S  V  L  A  S  Y  A  D  E  I  N  V
CAACAAAGAGATACTCAAGATCTACACGTCAGAGATAGTACCAGGAATAGCTGCAGGCAGCGGGAGAGCAGGAGGA
 N  K  E  I  L  K  I  Y  T  S  E  I  V  P  G  I  A  A  G  S  G  E  Q  E  D
CAACCTTGGCTCGTGCGCAATGGCCGACATCGAGTGCCTGCAGTCGCTATCCAGAAGAATCCATTTTGGCCGTTT
 N  L  G  S  C  A  M  A  D  I  E  C  L  Q  S  L  S  R  R  I  H  F  G  R  F
TGTCGCAGAGGCTAAATTTATCAGTGAGGGGGACAAGATTGTGGATCTGATCAAAAAGAGAGATGTGGAAGGCAT
 V  A  E  A  K  F  I  S  E  G  D  K  I  V  D  L  I  K  K  R  D  V  E  G  I
TGAGGCGCTCATCACAAACGCCGAGGTCGAAAAACGGATCTTGGACAGACTTCTGGAGAAGGGAAGGGCGTATGG
 E  A  L  I  T  N  A  E  V  E  K  R  I  L  D  R  L  L  E  K  G  R  A  Y  G
AACAGACCCGACACTAAAGTTCACGCAGCACATTCAGAGCAAGGTGAAGCCCGAGGTGATTGTGAAAATCTACAA
 T  D  P  T  L  K  F  T  Q  H  I  Q  S  K  V  K  P  E  V  I  V  K  I  Y  K
GGATTTCGTGATTCCGCTCACGAAGAAGGTCGAAGTCGACTACTTGCTGAGACGGCTGGAGGACGAGGAGGACGA
 D  F  V  I  P  L  T  K  K  V  E  V  D  Y  L  L  R  R  L  E  D  E  E  D  D
TGATGCGACGCAGAAAAGCGGCGGCTACGTTGACCGGTTTCTCTCCTCTGGCTTGTACTAGaaattaaaattttc
 D  A  T  Q  K  S  G  G  Y  V  D  R  F  L  S  S  G  L  Y
agtactttaattattctcgaattctagttcagataccgcatggtaatttcaaaggccagaaaagtggccgcgttg gctggggcagctctcagaatagtcggcgagaatcctttgactagcccccaggcaccgctctgtctccaaataccc ctaatagtctcaacagcatttctataaaccagcttcttgtagttgtccgtctgcatgttggacttgatcacatcg atcggataaatactgaaccacatcccgtaacctgccagcgccccaaagacgcagagcttccagttctcgatgtcc ttcctggcaatattccgcgactcgatctcgttttttcacgagagcttcaaaagtcagaaaatacgctccgctaccc aaactttctcttgccagcgtaggtcccagacccggtagattaacttgatgcctcccgtatggtacagcttcttg atcc
```

FIGURE 5

SEQUENCE LISTING

```
<160> NUMBER OF SEQ ID NOS: 7

<210> SEQ ID NO 1
<211> LENGTH: 843
<212> TYPE: DNA
<213> ORGANISM: Hansenula polymorpha
<220> FEATURE:
<221> NAME/KEY: CDS
<222> LOCATION: (1)..(843)
<223> OTHER INFORMATION:

<400> SEQUENCE: 1 atg gac ttt atg aag cca gaa aca gtg ctg gac ctt ggc aac att aga      48
Met Asp Phe Met Lys Pro Glu Thr Val Leu Asp Leu Gly Asn Ile Arg
1               5                   10                  15 gat gcc ttg gtc cgg atg gag gat acg atc atc ttc aac ttt atc gag      96
Asp Ala Leu Val Arg Met Glu Asp Thr Ile Ile Phe Asn Phe Ile Glu
                20                  25                  30 cgg tcg cag ttc tat gcg tcg ccc tcg gta tac aaa gtc aac cag ttc     144
Arg Ser Gln Phe Tyr Ala Ser Pro Ser Val Tyr Lys Val Asn Gln Phe
            35                  40                  45 cct att ccc aac ttc gac ggc tcg ttc ttg gac tgg ctg ttg tcg cag     192
```

```
cac gag cga atc cat tcg cag gtg agg aga tac gac gcg cca gac gag      240
His Glu Arg Ile His Ser Gln Val Arg Arg Tyr Asp Ala Pro Asp Glu
 65              70                  75                  80 gtg cct ttt ttc ccc aac gtg ctg gaa aaa acg ttt ctg ccc aag atc      288
Val Pro Phe Phe Pro Asn Val Leu Glu Lys Thr Phe Leu Pro Lys Ile
                 85                  90                  95 aac tac cca tcg gtg cta gcc tcc tac gcg gat gaa atc aac gtc aac      336
Asn Tyr Pro Ser Val Leu Ala Ser Tyr Ala Asp Glu Ile Asn Val Asn
            100                 105                 110 aaa gag ata ctc aag atc tac acg tca gag ata gta cca gga ata gct      384
Lys Glu Ile Leu Lys Ile Tyr Thr Ser Glu Ile Val Pro Gly Ile Ala
        115                 120                 125 gca ggc agc gga gag cag gag gac aac ctt ggc tcg tgc gca atg gcc      432
Ala Gly Ser Gly Glu Gln Glu Asp Asn Leu Gly Ser Cys Ala Met Ala
    130                 135                 140 gac atc gag tgc ctg cag tcg cta tcc aga aga atc cat ttt ggc cgt      480
Asp Ile Glu Cys Leu Gln Ser Leu Ser Arg Arg Ile His Phe Gly Arg
145                 150                 155                 160 ttt gtc gca gag gct aaa ttt atc agt gag ggg gac aag att gtg gat      528
Phe Val Ala Glu Ala Lys Phe Ile Ser Glu Gly Asp Lys Ile Val Asp
                165                 170                 175 ctg atc aaa aag aga gat gtg gaa ggc att gag gcg ctc atc aca aac      576
Leu Ile Lys Lys Arg Asp Val Glu Gly Ile Glu Ala Leu Ile Thr Asn
            180                 185                 190 gcc gag gtc gaa aaa cgg atc ttg gac aga ctt ctg gag aag gga agg      624
Ala Glu Val Glu Lys Arg Ile Leu Asp Arg Leu Leu Glu Lys Gly Arg
        195                 200                 205 gcg tat gga aca gac ccg aca cta aag ttc acg cag cac att cag agc      672
Ala Tyr Gly Thr Asp Pro Thr Leu Lys Phe Thr Gln His Ile Gln Ser
    210                 215                 220 aag gtg aag ccc gag gtg att gtg aaa atc tac aag gat ttc gtg att      720
Lys Val Lys Pro Glu Val Ile Val Lys Ile Tyr Lys Asp Phe Val Ile
225                 230                 235                 240 ccg ctc acg aag aag gtc gaa gtc gac tac ttg ctg aga cgg ctg gag      768
Pro Leu Thr Lys Lys Val Glu Val Asp Tyr Leu Leu Arg Arg Leu Glu
                245                 250                 255 gag gag gac gat gat gcg acg cag aaa agc ggc ggc tac gtt gac          816
Asp Glu Glu Asp Asp Asp Ala Thr Gln Lys Ser Gly Gly Tyr Val Asp
            260                 265                 270 cgg ttt ctc tcc tct ggc ttg tac tag                                  843
Arg Phe Leu Ser Ser Gly Leu Tyr
        275                 280

<210> SEQ ID NO 2
<211> LENGTH: 280
<212> TYPE: PRT
<213> ORGANISM: Hansenula polymorpha

<400> SEQUENCE: 2

Met Asp Phe Met Lys Pro Glu Thr Val Leu Asp Leu Gly Asn Ile Arg
1               5                   10                  15

Asp Ala Leu Val Arg Met Glu Asp Thr Ile Ile Phe Asn Phe Ile Glu
            20                  25                  30

Arg Ser Gln Phe Tyr Ala Ser Pro Ser Val Tyr Lys Val Asn Gln Phe
        35                  40                  45

Pro Ile Pro Asn Phe Asp Gly Ser Phe Leu Asp Trp Leu Leu Ser Gln
    50                  55                  60
```

```
His Glu Arg Ile His Ser Gln Val Arg Arg Tyr Asp Ala Pro Asp Glu
 65                  70                  75                  80

Val Pro Phe Phe Pro Asn Val Leu Glu Lys Thr Phe Leu Pro Lys Ile
                 85                  90                  95

Asn Tyr Pro Ser Val Leu Ala Ser Tyr Ala Asp Glu Ile Asn Val Asn
            100                 105                 110

Lys Glu Ile Leu Lys Ile Tyr Thr Ser Glu Ile Val Pro Gly Ile Ala
        115                 120                 125

Ala Gly Ser Gly Glu Gln Glu Asp Asn Leu Gly Ser Cys Ala Met Ala
    130                 135                 140

Asp Ile Glu Cys Leu Gln Ser Leu Ser Arg Arg Ile His Phe Gly Arg
145                 150                 155                 160

Phe Val Ala Glu Ala Lys Phe Ile Ser Glu Gly Asp Lys Ile Val Asp
                165                 170                 175

Leu Ile Lys Lys Arg Asp Val Glu Gly Ile Glu Ala Leu Ile Thr Asn
            180                 185                 190

Ala Glu Val Glu Lys Arg Ile Leu Asp Arg Leu Leu Glu Lys Gly Arg
        195                 200                 205

Ala Tyr Gly Thr Asp Pro Thr Leu Lys Phe Thr Gln His Ile Gln Ser
    210                 215                 220

Lys Val Lys Pro Glu Val Ile Val Lys Ile Tyr Lys Asp Phe Val Ile
225                 230                 235                 240

Pro Leu Thr Lys Lys Val Glu Val Asp Tyr Leu Leu Arg Arg Leu Glu
                245                 250                 255

Asp Glu Glu Asp Asp Ala Thr Gln Lys Ser Gly Gly Tyr Val Asp
            260                 265                 270

Arg Phe Leu Ser Ser Gly Leu Tyr
        275                 280

<210> SEQ ID NO 3
<211> LENGTH: 1655
<212> TYPE: DNA
<213> ORGANISM: Hansenula polymorpha
<220> FEATURE:
<221> NAME/KEY: gene
<222> LOCATION: (1)..(1655)
<223> OTHER INFORMATION: 1,8 kb genomic DNA-fragment from Hanseula
      polymorpha
<220> FEATURE:
<221> NAME/KEY: gene
<222> LOCATION: (1)..(1655)
<223> OTHER INFORMATION: 1,8 kb genomic DNA-fragment from Hansenula
      polymorpha

<400> SEQUENCE: 3
```
cccggcccaa tgccagcaat atggagacgt ttaggcagaa taggcgttcc atacttctca    60
cgctgcttgt tgccaccgga atatacaccg cattgcagtt tgcacacatc atactatatg   120
acgattacat tggcggaacg tatcgcgagt cgctcacgag acgcattaga atgacagaga   180
aatcgcgaaa cgaccttata gacgcacgtg aaaactacgg gtttggaggc agcaaggagg   240
agcgaatcca gcggttttg tggttcagac atctttcgtg gcttttaggc gaggataagc   300
gaacttgagg agcgtttttt ttttcctgtt tagttttgt aggtatggac tttatgaagc   360
cagaaacagt gctggaccctt ggcaacatta gagatgcctt ggtccggatg gaggatacga   420
tcatcttcaa ctttatcgag cggtcgcagt tctatgcgtc gccctcggta tacaaagtca   480
accagttccc tattcccaac ttcgacggct cgttcttgga ctggctgttg tcgcagcacg   540
agcgaatcca ttcgcaggtg aggagatacg acgcgccaga cgaggtgcct tttttcccca   600

```
acgtgctgga aaaaacgttt ctgcccaaga tcaactaccc atcggtgcta gcctcctacg    660
cggatgaaat caacgtcaac aaagagatac tcaagatcta cacgtcagag atagtaccag    720
gaatagctgc aggcagcgga gagcaggagg acaaccttgg ctcgtgcgca atggccgaca    780
tcgagtgcct gcagtcgcta tccagaagaa tccattttgg ccgttttgtc gcagaggcta    840
aatttatcag tgaggggac aagattgtgg atctgatcaa aaagagagat gtggaaggca    900
ttgaggcgct catcacaaac gccgaggtcg aaaaacggat cttggacaga cttctggaga    960
agggaagggc gtatggaaca gacccgacac taaagttcac gcagcacatt cagagcaagg   1020
tgaagcccga ggtgattgtg aaaatctaca aggatttcgt gattccgctc acgaagaagg   1080
tcgaagtcga ctacttgctg agacggctgg aggacgagga ggacgatgat gcgacgcaga   1140
aaagcggcgg ctacgttgac cggtttctct cctctggctt gtactagaaa ttaaaatttt   1200
cagtacttta attattctcg aattctagtt cagataccgc atggtaattt caaaggccag   1260
aaaagtggcc gcgttggctg ggcagctct cagaatagtc ggcgagaatc ctttgactag   1320
cccccaggca ccgctctgtc tccaaatacc cctaatagtc tcaacagcat ttctataaac   1380
cagcttcttg tagttgtccg tctgcatgtt ggacttgatc acatcgatcg gataaatact   1440
gaaccacatc ccgtaacctg ccagcgcccc aaagacgcag agcttccagt tctcgatgtc   1500
cttcctggca atattccgcg actcgatctc gttttcacg agagcttcaa aagtcagaaa   1560
atacgctccg ctacccaaac tttctcttgc cagcgtaggt cccagacccc ggtagattaa   1620
cttgatgcct cccgtatggt acagcttctt gatcc                               1655
```

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
aattaaccct cactaaaggg                                                 20

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide

<400> SEQUENCE: 5
gtaatacgac tcactatagg gc                                              22

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide

<400> SEQUENCE: 6
atatagatct acaaaaacta aacagg                                          26

<210> SEQ ID NO 7
<211> LENGTH: 28
<212> TYPE: DNA
<213> ORGANISM: Artificial Sequence
<220> FEATURE:

```
-continued

<223> OTHER INFORMATION: Oligonucleotide

<400> SEQUENCE: 7
atatagatct gatgcgacgc agaaaagc                                              28
```

NUCLEIC ACID MOLECULE, COMPRISING A NUCLEIC ACID CODING FOR A POLYPEPTIDE WITH CHORISMATE MUTASE ACTIVITY

CROSS-REFERENCE TO RELATED APPLICATIONS

The present application is a Continuation of International Patent Application No. PCT/EP00/03844, filed on Apr. 27, 2000, which claims priority of German Patent Application No. 199 19 124.7, filed on Apr. 27, 1999.

The present invention concerns a nucleic acid molecule, comprising a nucleic acid coding for a polypeptide with chorismate mutase activity and derivatives thereof, wherein the derivatives show at least 10% of the chorismate mutase activity of the chorismate mutase according to SEQ ID NO: 2. The invention further concerns vectors containing nucleic acid molecules, host cells containing nucleic acid molecules and processes for the production of polypeptides with chorismate mutase activity. The present invention further concerns the polypeptides with chorismate mutase activity and antibodies which specifically recognise these. In addition, the invention concerns processes for the production of auxotrophic yeast strains by means of the nucleic acid molecules and the use thereof in processes for the recombinant expression of heterologous genes.

BACKGROUND OF THE INVENTION

As single-cell, eukaryotic microorganisms, yeasts can be cultured without difficulty and have the great advantage of being readily genetically manipulable. Also, they can process and modify recombinant proteins in accordance with the patterns known from higher organisms. As far as is yet known, they contain no pathogenic substances and are therefore also suitable for the production of therapeutic proteins. Thus for example the first vaccine produced by heterologous gene expression, the hepatitis B vaccine, was *heterologously* expressed in the well-characterised baker's yeast *Saccharomyces cerevisiae* (Lepetic et al., 1996).

While *S. cerevisiae* makes it possible to produce many different proteins (for a review, see Gellissen and Hollenberg, 1997), there are nonetheless also a few limiting properties. Thus for example the maximal content of heterologous protein is about 1–5% of the total protein content of the cell (Buckholz and Gleeson, 1991).

Various other yeasts, such as for example *Schizosaccharomyces pombe*, *Kluyveromyces lactis*, *Yarrowia lipolytica* and also *Hansenula polymorpha* have been characterised and compared with *S. cerevisiae* in terms of their suitability as expression systems (Müller et al., 1998). All these yeasts showed markedly stronger secretion of active protein than *S. cerevisiae*, the heterologous gene expression being dependent on the particular gene, but independent of the donor organism. Basically, methylotrophic yeasts are found to be attractive organisms for the production of recombinant proteins. The methylotrophic yeasts are subdivided into the four genera *Hansenula*, *Pichia*, *Candida* and *Torulopsis*, which all possess the ability to utilise methane, methylamine, formaldehyde or formate as carbon and energy source.

Inter alia, the yeast *Hansenula polymorpha* from the *Saccharomycetaceae* family (Lodder, 1970) belongs to the relatively small group of the methylotrophic yeasts. *Hansenula polymorpha* does not ferment glucose under aerobic conditions, and is thus Crabtree-negative (Verduyn et at., 1992) and with a growth temperature optimum of 37° C. is classed among the thermotolerant yeasts; thus it is an exception among the *methylotrophic* genera. The natural habitat of the methylotrophic yeasts is locations rich in organic material.

Hitherto, only a few genes of the yeast *Hansenula polymorpha* had been cloned and characterised (Hansen and Hollenberg, 1996), and according to GenBank the number of cloned genes in *Hansenula polymorpha* amounts to >30. However, how many of these are thoroughly characterised or are suitable as marker genes for plasmid selection, is unknown to me. Hence, I would suggest that similarities of these genes with the homologous genes in *Saccharomyces cerevisiae*, insofar as these are present, are relatively limited (Dobson et al., 1982). The key enzymes in methylotrophic metabolism are the enzymes methanol oxidase (MOX), dihydroxyacetone synthase (DAS) and formate dehydrogenase (FMD), whose controlled expression by very strongly regulated promoters opens up a variety of useful possibilities for heterologous gene expression. These facts make *Hansenula polymorpha* an industrially interesting organism (Gellissen et al., 1994).

So far, only two auxotrophic strains of *H. polymorpha* are available, whose transformation can be selected by functional complementation of ura3- or leu2-deficiency respectively. The provision of farther transformation systems, consisting of auxotrophic strains and of nucleic acids capable of complementing the auxotrophy hitherto failed because suitable genes capable of this complementation were not available. While a number of genes from the amino acid or nucleic acid biosynthesis pathway of the baker's yeast *S. cerevisiae* were known, it had nonetheless in the past been found that the differences between the genes of baker's yeast and the methylotrophic yeasts are sometimes considerable. Hence it cannot in general be expected that a *S. cerevisiae* gene will be suitable for complementation of an auxotrophy in a methylotrophic yeast, nor can it be expected that genes from a methylotrophic yeast will be capable of complementing an auxotrophy in *S. cerevisiae*.

Hence a technical problem underlying the present invention is to provide a new gene from *H. polymorpha*, which can serve as a selectable marker for complementation in the transformation of suitable auxotrophic yeast strains. A further problem consists in the provision of vectors and host cells, which contain the gene. Further, it is to provide the polypeptide encoded by the gene and antibodies which specifically recognise the polypeptide. Finally, it is to provide suitable auxotrophic strains.

BRIEF SUMMARY OF THE INVENTION

This problem is solved according to the invention by a nucleic acid molecule comprising a nucleic acid coding for a polypeptide with chorismate mutase activity or the complementary strand thereof, wherein the nucleic acid is selected from
  (a) a nucleic acid with the DNA sequence stated in SEQ ID NO:1 or the RNA sequence corresponding thereto;
  (b) a nucleic acid which hybridises with the complementary strand of a nucleic acid according to (a);
  (c) a nucleic acid which on the basis of the genetic code is degenerate to the DNA sequences defined under (a) and (b);
  (d) a nucleic acid which hybridises with one of the nucleic acids stated in (a) to (c) and the complementary strand thereof codes for a polypeptide with chorismate mutase activity;

(e) a nucleic acid which is at least 60% homologous to one of the nucleic acids stated in (a) to (d);

(f) a variant of the nucleic acids stated in (a) to (e), wherein the variant had additions, deletions, insertions or inversions relative to the nucleic acids stated in (a) to (e);

(g) a fragment of one of the nucleic acids stated in (a) to (f);

(h) a combination of several of the nucleic acids stated in (a) to (g), wherein the polypeptide encoded by the nucleic acid or complementary strand thereof has at least 10% of the chorismate mutase activity of the chorismate mutase according to SEQ ID NO:2.

In microorganisms and plants, the biosynthesis of aromatic amino acids proceeds firstly through 7 enzyme-catalysed reactions of the shikimate pathway from erythrose-4-phosphate and phosphoenol pyruvate to chorismate (FIG. 1). Chorismate is the substrate of the first branching point. In the baker's yeast Saccharomyces cerevisiae, starting from this branching point, on the one hand anthranilate is formed via the enzyme anthranilate synthase (E.C. 4.1.3.27), and on the other prephenate via the enzyme chorismate mutase (E.C. 5.4.99.5). Finally, via further intermediate products, tyrosine and phenylalanine are formed from prephenate (Braus, 1991). In the baker's yeast Saccharomyces cerevisiae, the chorismate mutase is encoded by the ARO7 gene (Schmidheini et al., 1989), which is located on chromosome XVI. ARO7 encodes a 0.95 kb mRNA and contains a 771 bp open reading frame, which codes for a protein consisting of 256 amino acids. The present invention will be understood to include all chorismate mutases, including fragments, variants and homologs thereof, except for Saccharomyces cerevisiae ARO7 chorismate mutase.

Below, a number of terms are explained in more detail, in order to make clear how they should be understood in connection with the present application.

DETAILED DESCRIPTION

The term "chorismate mutase", as used below in the description, includes complete chorismate mutase, chorismate mutase fragments, chorismate mutase mutants and fusion proteins thereof. Polypeptides which have at least 10% of the chorismate mutase activity of the chorismate mutase according to SEQ ID NO:2 are regarded as being according to the invention.

"Chorismate mutase activity" means the catalytic conversion of chorismate to prephenate as part of the phenylalanine and tyrosine biosynthesis which is catalysed by the enzyme chorismate mutase [E.C. 5.4.99.5]. The chorismate mutase activity of the polypeptide according to the invention can for example be measured spectrophotometrically through the acid-catalysed conversion of the product prephenate to phenylpyruvate, which absorbs at 320 nm (Schmidheini et al., 1989).

For its growth or proliferation, a "prototrophic" microorganism needs only simple nutrients (carbon and nitrogen) and minerals, but can itself build up all needed amino acids. Hence it is capable of growing on "minimal medium".

In contrast to this, "auxotrophic" microorganisms need additional factors, for example amino acids, which they cannot themselves synthesise owing to a defect in the biosynthesis pathway for the factor concerned. In connection with the present invention, the auxotrophy is preferably a phenylalanine/tyrosine auxotrophy, which is caused through diminished or absent chorismate mutase activity, e.g. of an auxotrophic yeast strain prepared according to the invention.

"Minimal medium" means a nutrient solution, which contains only the components which are necessary for the growth of a prototrophic microorganism. In connection with the present invention, the minimal medium is preferably a phenylalanine-and/or tyrosine-free medium, through which the selection of the phenylalanine/tyrosine auxotrophic form of the micro-organism compared to the prototrophic form of the microorganism is made possible.

"His" tag means a sequence of at least 6 histidine amino acids, which by appropriate cloning and fusion with an expressible sequence leads to a fusion protein with at least 6 His residues at the $NH_2$ terminus, which can easily be purified by complexing with a $Ni^{2+}$ column.

A "heterologous gene" is understood to mean the coding region of a structural gene, which is either not expressed under the control of its own (homologous) promoter or not in the organism from which it is derived, or else is expressed neither under the control of its own promoter nor in the original organism.

"Cloning" is intended to include all cloning methods known in the state of the technology, which could be used here, which are however not all described in detail, since they are among the obvious tools of the skilled person.

"Recombinant expression in a suitable host cell" is to be understood to mean all expression methods known in the state of the technology in known expression systems, which could be used here, which are however not all described in detail, since they are among the obvious tools of the skilled person.

By selection and sequencing of a genomic clone from Hansenula polymorpha which after transformation is capable of functionally complementing the phenylalanine/tyrosine auxotrophy of the Saccharomyces cerevisiae aro7Δ-deletion strain, the inventors have for the first time succeeded in identifying a nucleic acid according to the invention, and producing auxotrophic mutants of methylotrophic yeasts with this nucleic acid. Thus a further urgently needed transformation system for methylotrophic yeasts is provided, which makes the targeted selection of transformed yeasts with simple media possible.

The inventors have prepared a genomic bank from H. polymorpha by cloning of restriction fragments of chromosomal H. polymorpha DNA into a shuttle vector, the said shuttle vector having a high copy number in yeast and the Hansenula genes being expressed in S. cerevisiae under the control of their endogenous promoter. This genomic bank was used for the complementation of auxotrophic Saccharomyces cerevisiae strains, although it was not known each endogenous promoter of Hansenula polymorpha is active in S. cerevisiae.

Surprisingly, it was now found that the chorismate mutase gene from Hansenula polymorpha is transcribed and translated in S. cerevisiae and is enzymatically active.

For several reasons, it was not to be expected that the chorismate mutase gene in particular could be expressed in Saccharomyces cerevisiae.

Thus it was not known whether the chorismate mutase gene from H. polymorpha contains introns and whether the S. cerevisiae splicing apparatus is capable of the correct processing of the possible pre-RNA. From now on, it could be shown that the chorismate mutase gene from H. polymorpha has no introns.

Further, it could not be foreseen that the translation product can be correctly folded and if necessary assembled in *S. cerevisiae*, in order to give a sufficiently active chorismate mutase which is capable of catalysing the reaction of chorismate to prephenate. The absence of predictability is supported by the fact that HLEU2, the LEU2 homologue from *H. polymorpha*, is not capable of complementing a corresponding mutation in *S. cerevisiae* (Agaphonov et al., 1994).

Further, it was not known that the biosynthesis of the aromatic amino acids tyrosine and phenylalanine in *H. polymorpha* involves the conversion of chorismate to prephenate with the aid of the enzyme chorismate mutase at all. In fact it is known that there are considerable differences in the biosynthesis of aromatic amino acids. Thus in some cyanobacteria prephenate is first converted to arogenate by transamination. This pathway is also used by plants (Jensen and Stenmark, 1975) and is more widespread in nature than the hydroxy-phenylpyruvate/phenylpyruvate pathway, which is used by *Saccharomyces cerevisiae* and *E. coli*.

The nucleic acid contained in the nucleic acid molecule according to the invention can be genomic DNA, cDNA or synthetic DNA, where a synthetic DNA sequence is also understood to mean one such which contains modified internucleoside bonds. Furthermore the nucleic acid can be an RNA sequence, which e.g. can be necessary for expression by means of recombinant vector systems. The nucleic acid according to (b) is for example obtainable by use of a detectably labelled probe which corresponds to one of the sequences stated in (a) or a fragment or complementary strand thereof, for the screening of cDNA or genomic DNA libraries from microorganisms. Preferably the microorganism from which the bank is created belongs to a genus selected from: *Pichia, Hansenula, Candida, Torulopsis, Saccharomyces, Schizosaccharomyces, Kluyveromyces* and *Yarrowia*. In particular, the microorganism belongs to a species selected from: *Hansenula polymorpha, Saccharomyces cerevisiae, Schizosaccharomyces pombe, Kluyveromyces lactis* and *Yarrowia lipolytica*. In this, the identification of positive cDNA or genomic DNA clones is performed according to standard procedures. See Maniatis et al., Molecular Cloning (1989), Cold Spring Harbor Laboratory Press.

In a preferred embodiment, the hybridisation stated under (b) or (d) is performed under stringent conditions. Stringent hybridisation conditions are e.g. incubation at 65° C. overnight in 7% SDS, 1% BSA, 1 mM EDTA, 250 mM sodium phosphate buffer (pH 7.2) and subsequent washing at 65° C. with 2×SSC; 0.1% SDS.

In a preferred embodiment, nucleic acids are provided which are at least 60% homologous to the nucleic acid sequence stated in (a). Preferred are nucleic acids at least 80% homologous to the nucleic acid sequence stated in (a). Especially preferred are nucleic acids at least 90% or 95% homologous to the nucleic acid sequence stated in (a).

According to the invention, the expression "homology" means homology at the DNA level, which can be determined by known procedures, e.g. computer-aided sequence comparisons (Basic local alignment search tool, S. F. Altschul et al., J. Mol. Biol. 215 (1990), 403–410).

The expression "homology", well-known to the skilled person, designates the degree of relatedness between two or more nucleic acid molecules, which is determined by the agreement between the sequences. The "percentage homology" is obtained from the percentage of identical regions in two or more sequences taking account of gaps or other sequence features.

The homology of mutually related nucleic acid molecules can be determined by means of known procedures. As a rule, special computer programs with the algorithms taking account of the special requirements are used.

Preferred procedures for the determination of homology firstly generate the greatest agreement between the sequences studied. Computer programs for determination of homology include, but are not limited to, the GCG program package, including GAP (Devereux, J., et al., Nucleic Acids Research 12 (12): 387 (1984); Genetics Computer Group University of Wisconsin, Madison, (Wis.)); and BLASTP, BLASTN and FASTA (Altschul S., et al., J. Mol. Biol., 215: 403–410 (1990)). The BLASTX program can be obtained from the National Centre for Biotechnology Information (NCBI) and from other sources (BLAST Handbook, Altschul S., et al., NCB NLM NIH Bethesda Md. 20894; Altschul S., et al., J. Mol. Biol., 215: 403–410 (1990)). The well-known Smith-Waterman algorithm can also be used for the determination of homologies.

Preferred parameters for the nucleic acid sequence comparison include the following:
Algorithm: Needleman and Wunsch, J. Mol. Biol. 48: 443–453 (1970)
Comparison matrix:
  Matches=+10
  Mismatches=0
Gap penalty 50
Gap length penalty: 3

The GAP program is also suitable for use with the above parameters. The above parameters are the default parameters for nucleic acid sequence comparisons.

Further examples of algorithms, gap opening penalties, gap extension penalties and comparison matrices including those named in the program handbook, Wisconsin package, Version 9, September 1997, can be used. The choice will depend on the comparison to be performed and further on whether the comparison is performed between sequence pairs, when GAP or Best Fit are preferred, or between one sequence and a large sequence database, when FASTA or BLAST are preferred.

An agreement of 60% determined with the aforesaid algorithm is described in the context of the present application as 60% homology. The same applies for higher degrees of homology.

In a preferred embodiment, the nucleic acid according to the invention is a combination of several of the nucleic acids stated under (a) to (f), which can be obtained by the fusion and if necessary cloning known to the skilled person. These combinations can e.g. be of especial interest for the creation of immunogenic constructs.

In a further preferred embodiment, the polypeptide encoded by the nucleic acid according to the invention has at least 50% of the chorismate mutase activity of the chorismate mutase SEQ ID NO:2. It is especially preferred that the polypeptide has at least 75% of the chorismate mutase activity according to SEQ ID NO:2. Here, as already stated, the chorismate mutase activity is measured after Schmidheini et al., 1989.

In a further embodiment, the nucleic acid molecule comprises a promoter suitable for its expression, the nucleic acid being under the control of the promoter. The choice of the promoter depends on the expression system used for expression, in particular on the choice of host organism. Preferred according to the invention are both constitutive promoters such as PGK-and G3PDH-promoters and also inducible promoters such as GAL4, ADH2 and the Cu-metallothionein promoter (survey in Recombinant Gene Expression Protocols in Methods in Molecular Biology Vol. 63, Ed. R S Tuan, Chapter III; Schena, M. et al. (1991) Vectors for constitutive and inducible expression in yeast, Methods in Enzymol. 194, 389–398). Further, the use of mammalian glucocorticoid response elements (GRE) for increasing transcription is also taken into account by the invention (Schena et al., Science 241 (1988), 965–967).

Also preferred are the promoters of the methanol metabolism of methylotrophic yeasts, in particular *Hansenula polymorpha*. The genes for the methanol metabolism enzymes in *Hansenula polymorpha* are among the most strongly expressed and regulated genes that have so far been described in yeasts (Van der Klei et al., 1991). The corresponding proteins can comprise up to 30% of the total protein content of the cell (Janowicz et al., 1985; Ledeboer et al., 1985). The expression of the methanol metabolism genes can on the one hand be induced by methanol, on the other hand however, the presence of glycerol also leads to derepression. Thus in this way the strong promoters of the methanol metabolism can also be used for heterologous gene expression under methanol-free culture conditions.

Especially preferred promoters are the methanol oxidase MOX-promoter described in *H. polymorpha*, which at about 1.5 kb is unusually large and is among the strongest yeast promoters so far described. The presence of glucose leads to repression of the MOX-promoter, however the activity of this promoter can be increased more than 1000-fold by glycerol or methanol (Gödecke et al., 1994). Further especially preferred is the dihydroxy-acetone synthase DAS-promoter (Ledeboer et al., 1985) and the FMD-promoter (European Patent 299108).

In a further preferred embodiment, the nucleic acid molecule also comprises a signal peptide-coding nucleic acid sequence, which ensures the export of the expressed protein, where the signal peptide-coding nucleic acid sequence is preferably directly 5' bound to the heterologous gene to be expressed. For the secretion and modification of many eukaryotic proteins, it is necessary to fuse the protein sequence at the N-terminus with a signal sequence, in order to steer the polypeptides into the secretion apparatus. Possible for this are for example components from the *S. occidentalis* gene GAM1 (Dohmen et al., 1990) and from a hormone gene of the crab *Carcinus maenas* (Weydemann et al., 1989), which were successfully used for the secretion of hirudin (Weydemann et al., 1995).

In a further preferred embodiment, the nucleic acid molecule also comprises at least a part of a vector, in particular control regions, wherein the vector can be selected from: bacteriophages such as λ-derivatives, plasmids, adenoviruses, vaccinia viruses, baculoviruses, SV40 viruses and retroviruses, preferably MoMuLV (Moloney Murine Leukemia Virus).

Especially preferred are yeast transformation vectors, both integrative yeast plasmids (YIp) and also extrachromosomal plasmid vectors being possibilities. The extrachromosomal plasmid vectors subdivide into episomal yeast plasmids (YEp), replicative yeast plasmids (YRp) and yeast centromer plasmids (YCp) (see Singh, K. K. and Heinemann, J. A., Chapter 11 in Recombinant Gene Expression Protocols, v. supra). Further, artificial yeast chromosomes (YACs) are also possible as expression vectors according to the invention.

Also especially preferred vectors are yeast replication plasmids, which contain a replication origin ori and an antibiotic resistance cassette, so that they can be propagated and selected in *E. coli*. Furthermore, they bear an ARS sequence for chromosomally independent replication in the yeast cell, such as for example HARS1 from *H. polymorpha*, and a metabolic yeast selection marker, such as for example URA3 or HLEU2 (Gellisen and Hollenberg, 1997).

Many heterologous proteins have already been produced in *H. polymorpha* (Gellissen and Hollenberg, 1997) and by the placement of more than one expression cassette on one transformation vector, co-expression of different genes is also possible (Gilbert et al., 1994).

Further, a nucleic acid molecule is preferred which in addition comprises a His-tag coding DNA sequence, which on expression of the construct leads to the formation of a fusion protein with a His-tag at the $NH_2$ terminus, which facilitates the purification of the protein on a nickel column through chelate formation.

According to the invention, host cells are provided, which contain the nucleic acid molecule and which are suitable for the expression of the heterologous gene. In the state of the technology, many prokaryotic and eukaryotic expression systems are known, where the host cells are for example selected from prokaryotic cells such as *E. coli* or *B. subtilis*, from eukaryotic cells such as yeast cells, insect cells and mammalian cells, e.g. CHO cells, COS cells or HeLa cells, and derivatives thereof In the state of the technology for example, certain CHO production lines are known whose glycosylation patterns are altered compared to CHO cells.

Preferably, the yeast belongs to a genus selected from: *Pichia, Hansenula, Candida, Torulopsis, Saccharomyces, Schizosaccharomyces, Kluyveromyces* and *Yarrowia*. In particular, the microorganism belongs to a species selected from: *Hansenula polymorpha, Saccharomyces cerevisiae, Schizosaccharomyces pombe, Kluyveromyces lactis* and *Yarrowia lipolytica* (see Recombinant Gene Expression Protocols in Methods in Molecular Biology, above).

A further object of the present invention is a process for the production of a polypeptide with chorismate mutase activity. For this, the nucleic acid molecule according to the invention is expressed in a suitable host cell and the protein isolated from the host cell or the medium by standard procedures.

Many procedures for the expression of DNA sequences are known to the skilled person; see Recombinant Gene Expression Protocols in Methods in Molecular Biology, above. The expression can be both constitutive and also inducible, inducers such as for example IPTG and $Zn^{2+}$ being known to the skilled person. The polypeptide with chorismate mutase activity produced can, if a His-tag was fused to the $NH_2$ terminus of the polypeptide, be purified by chelate formation on a nickel column. Preferably the polypeptide with chorismate mutase activity is purified by ion exchange chromatography and/or gel filtration chromatography. The implementation of these measures is well-known to the skilled person.

In a further preferred embodiment, the polypeptide with chorismate mutase activity produced according to the invention is modified. Here the modifications include the di-, oligo- and polymerisation of the monomeric starting product for example through crosslinking, e.g. with dicyclohexyl-carbodiimide or pegylation or association (self-assembly). Other modifications include side-chain modifications, for example of ε-amino-lysine residues of the polypeptide, or amino- or carboxy-terminal modifications. Other modifications include posttranslational events, e.g. the glycosylation or the partial or complete deglycosylation of the protein.

In a preferred embodiment, the polypeptide obtained in recombinant expression in prokaryotes or glycosylation-deficient eukaryotes is non-glycosylated. Also taken into account according to the invention is a polypeptide with chorismate mutase activity which is glycosylated by recombinant expression in eukaryotes capable of glycosylation such as yeast cells, insect cells or mammalian cells, such as CHO cells or HeLa cells.

In a further embodiment, polypeptides with chorismate mutase activity are made available, which include an amino acid sequence, the amino acid sequence being encoded by one or several of the nucleic acid molecules according to the invention.

Preferably, polypeptides with chorismate mutase activity are made available, which comprise the amino acid sequence in SEQ ID NO:2 or a fragment thereof, which has at least 10% of the chorismate mutase activity of the chorismate mutase according to SEQ ID NO:2, preferably more than 50% and especially preferably more than 75%.

In a further embodiment, the invention provides polypeptides with chorismate mutase activity, obtainable by the recombinant production process or modifications thereof Further, non-glycosylated and glycosylated polypeptide with chorismate mutase activity, obtainable by expression in host cells capable or incapable of glycosylation, is provided. Depending on the intended use of the polypeptide, the glycosylation pattern of yeast, in particular methylotrophic yeast such as *Hansenula polymorpha*, of COS or HeLa cells can be preferred.

The invention further provides antibodies which specifically react with the polypeptide with chorismate mutase activity according to the invention and are obtainable by immunisation of an experimental animal with the polypeptide. Polyclonal antibodies can be obtained by immunisation of for example rabbits, mice or rats and subsequent extraction of antisera. Monoclonal antibodies can be obtained by standard procedures by immunisation of e.g. mice, extraction and immortalisation of the spleen cells and cloning of the hybridomas which produce antibodies specific for the polypeptide.

In a further embodiment, the invention provides a process for the production of a phenylalanine and tyrosine-auxotrophic yeast strain, comprising the destruction of the endogenous chorismate mutase gene of the corresponding yeast strain, wherein the mutant displays less than 10% of the chorismate mutase activity of the chorismate mutase according to SEQ ID NO:2.

According to the invention, homologous recombination is possible as a procedure for the production of the mutant. The disruption of the chorismate mutase gene by homologous recombination is based on the replacement of the endogenous chromosomal copy of the gene by an inactivated copy. For the preparation of a disruption construct, the cloning of larger regions of the gene to be destroyed, is necessary for the efficient homologous recombination, preferably including the 5' and 3' regions. The cloned regions should preferably cover at least 2 kb.

A BglII digestion of genomic DNA from *Hansenula polymorpha* and subsequent Southern Blot analysis with a chorismate mutase-specific probe such as e.g. SEQ ID NO:3 gave two band of 3.2 kb and 3.0 kb respectively. Further investigation showed that the 3.2 kb BglII/BglII fragment includes 690 bp of SEQ ID NO:3 and contains the flanking 5' region. The 3.0 kb BglII fragment includes 960 bp of SEQ ID NO:3 and contains the flanking 3' region. The isolation and directed fusion of the 3.2 kb fragment with the 3.0 kb fragment by means of standard procedures known to the skilled person leads to a 6.2 kb fragment, which includes the chorismate mutase gene and large 5' and 3' flanking regions.

According to the invention, the nucleic acid to be destroyed, preferably a nucleic acid according to SEQ ID NO:1 or a nucleic acid homologous thereto, especially preferably the nucleic acid according to SEQ ID NO:3 or a nucleic acid homologous thereto, in particular the nucleic acid including the 6.2 kb genomic DNA fragment, a nucleic acid homologous thereto or parts thereof, is cloned and mutated by oligonucleotide exchange, wherein the mutation can include additions, deletions, inversions or substitutions, which decrease the expression of the gene or lead to an inactive translation product. The mutation preferably takes place in at least one region or parts thereof, which are selected from the nucleic acid positions corresponding to the amino acid positions (SEQ ID NO:2) 10 to 20, 154 to 167, 192 to 196 and 240 to 247; these regions supposedly form the catalytic centre of the chorismate mutase. It is preferable to inactivate the nucleic acid coding for the chorismate mutase by cloning in a longer oligonucleotide.

Preferably the endogenous chorismate mutase gene is present as a single copy gene.

Preferably the oligonucleotide used for the oligonucleotide exchange comprises at least one selectable marker such as an antibiotic resistance or a metabolic marker. According to the invention, all selectable markers known in the state of the technology are included. Alternatively, the construct can also be prepared synthetically. For efficient homologous recombination, the construct should have a length of at least 2 kb.

The cloned-in oligonucleotide is flanked both 5' and 3' by chorismate mutase-specific fragments, whose sequences correspond to the sequences stated in claim 1(a) to 1(h) or are complementary to these and can hybridise with the original chromosomal copy.

The construct is first linearised for the production of a disruption mutant. Next, the prototrophic yeast strain intended for the production of the disruption mutant is transformed with the construct. Since the construct comprises a selectable marker, the transformants are selected by appropriate selection pressure. The phenylalanine/tyrosine-auxotrophic transformants are identified by growth on phenylalanine/tyrosine-free medium.

In a preferred embodiment, the process comprises the steps:

a) Preparation of a construct comprising at least two fragments of a nucleic acid according to claim 1(a) to 1(h) suitable for homologous recombination, which flank a nucleic acid unsuitable for homologous recombination;

b) Transformation of cells of a yeast strain with an intact endogenous chorismate mutase gene with this construct and c) Identification of the phenylalanine and tyrosine-auxotrophic transformants.

Especially preferably, the construct also comprises a selection marker gene. Further the construct can comprise one or several recombination sites, which preferably 5' and 3' flank the selectable marker and make possible the excision of the selectable marker from the construct after disruption of the endogenous chorismate mutase gene has been effected.

Preferably the recombination site is loxP. In an especially preferred embodiment, the process further includes in step b) that the cells of the yeast cells in step b) are brought into contact with nucleic acid suitable for the expression of Cre-recombinase, as a result of which the excision of the selectable marker by means of the loxP/Cre-recombinase system is made possible.

In an especially preferred embodiment, the yeast strain is *Hansenula polymorpha*.

In a further embodiment, the invention provides a phenylalanine and tyrosine-auxotrophic yeast strain, such as is obtainable e.g. by the process according to the invention.

In a further embodiment, a process for the recombinant production of proteins is provided, which includes:

a) Transformation of an auxotrophic yeast strain according to the invention with a combination of a nucleic acid according to the invention suitable for expression and a heterologous gene suitable for expression under the control of a suitable promoter;

b) Culturing of the transformants under conditions suitable for the expression of the heterologous gene and of the nucleic acid molecule according to the invention and if necessary isolation of the protein which is encoded by the heterologous gene.

In a preferred embodiment, the process further includes the step of the selection of the transformants on a phenylalanine and/or tyrosine deficient medium.

The recombinant production process according to the invention can be performed with nucleic acid molecule according to the invention and heterologous gene spatially separate from one another, where the two can be provided in two vectors (binary vector system) and can be transformed independently of one another. Alternatively, the nucleic acid molecule according to the invention, which codes for a polypeptide with chorismate mutase activity, and the heterologous gene are present in one vector. These cointegrate vectors have the advantage that the selectable marker gene and the heterologous gene are covalently bound to one another, so that all prototrophic clones after transformation also contain the heterologous gene, as a result of which the effort of screening is reduced.

Promoters and vectors preferred according to the invention for the expression of the heterologous gene correspond to the promoters and vectors stated above for the expression of the nucleic acid molecule according to the invention. The vector optionally also contains a signal peptide-coding nucleic acid sequence, which causes the secretion of the recombinant protein into the medium, and which is directly 5' bound to the heterologous gene. Also advantageous is the addition of a His-tag coding nucleic acid sequence to the 5' end of the heterologous gene, which after recombinant expression makes purification on a nickel chelate column possible.

The invention further provides recombinant proteins which are obtainable by the process stated above.

It is intended to illustrate the invention with the following figures and examples, but in no way to limit it. On the basis of the description and the examples, other embodiments are accessible to the skilled person, which are also included.

BRIEF DESCRIPTION OF THE DRAWINGS

FIG. 5 shows the sequence of a genomic 1.8 kb fragment (SEQ ID NO:3) which is capable of complementing the phenylalanine/tyrosine auxotrophy of the S. cerevisiae aro7Δ selection strain. The 5' and 3' region are shown in small letters, the open reading frame (SEQ ID NO:1) and the primary sequence (SEQ ID NO:2) of the derived gene product in large letters.

This is possible, since the primers OLSK34 and OLSK35 contain BglII recognition sequences.

Figure 7:
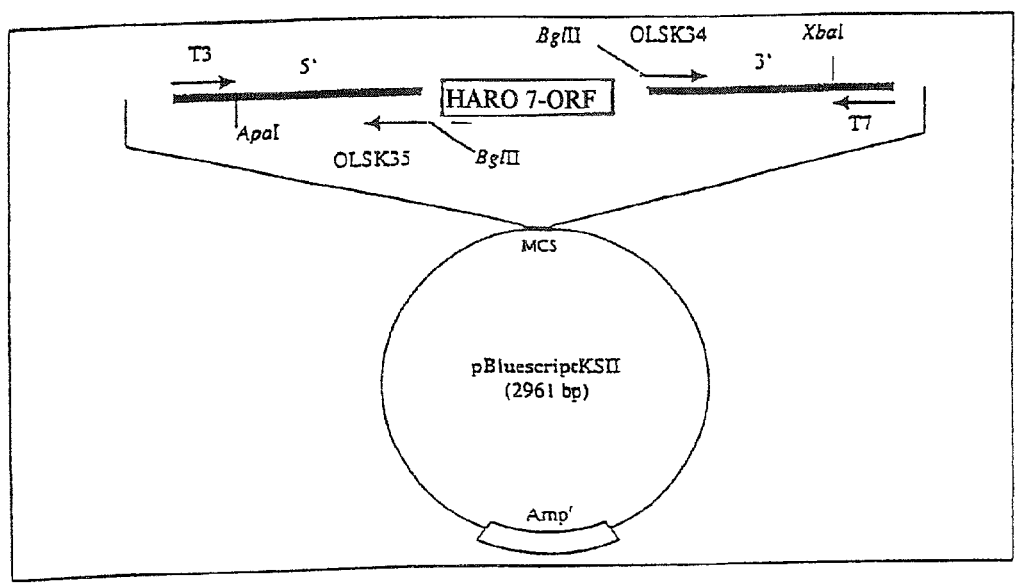

FIG. 7 shows the production of various deletion constructs. The flanking regions of the HARO7-ORF were ligated into the ApaI/XbaI cleaved vector pBluescriptKSII as ApaI/BglII and BglII/XbaI fragments respectively. The vector pBluescript II KS is marketed by the firm Stratagene, USA. The vector was again opened with BglII and the disruption cassettes cleaved with BamHI and BglII respectively were ligated in.

MATERIALS AND METHODS

1. Material 1.1 Chemicals

Chemicals for the preparation of solutions, buffers and media were obtained from the firms Merck (Darmstadt, Germany), Boehringer Ingelheim Bioproducts (Heidelberg, Germany), Carl Roth GmbH & Co KG (Karlsruhe, Germany), Gibco BRL (Life Technologies GmbH, Karlsruhe, Germany), Fluka (Neu-Ulm, Germany) and Sigma-Aldrich Chemie GmbH (Steinheim, Germany). Restriction enzymes, DNA-modifying enzymes and polymerases were purchased from MBI Fermentas (Vilnius, Lithuania) and RNase A from Boehringer Mannheim GmbH (Mannheim, Germany). As the DNA size standard the "1 kb DNA-ladder" (Gene Ruler Plus) from MBI Fermentas was used. Agarose was obtained from Roth. For the preparation of plasmid DNA from Escherichia coli and for the extraction of DNA from agarose gels, Kits from the firm Qiagen (Hilden, Germany) were used. Synthetic oligonucleotides were purchased from Nucleic Acid Products Supply Göttingen GmbH (Göttingen, Germany) and Gibco BRL (Life Technologies GmbH, Karlsruhe, Germany). Contract sequencing was performed by the firm MWG-Biotech GmbH (Ebersberg, Germany).

1.2 Strains, Plasmids and Oligonucleotides

For cloning, the E. coli strain DH5α [F', φ80dlacZΔM15, Δ(lacZYA-argF), U169, deoR, recA1, endA1, hsdR17, ($r_K-$, $m_K^+$), supE44, λ-, thi-1, gyrA96, relA1] was used (Woodcock, 1989). For this work, the H. polymorpha strain RB11 (ura3) was used (Weydemann et al., 1995).

The *S. cerevisiae* strains used are set out in table 1.

The plasmids and oligonucleotides needed for this work are listed in tables 2 and 3.

TABLE 1

*S. cerevisiae* strains used

| Strain | Genotype | Reference |
|---|---|---|
| RH 2185 | MAT αΔaro7::LEU2 suc2-δ9 ura3-52 leu2-3 leu2-112 his4-519 | Schnappauf et al., 1997 |
| RH 1405 | MAT α suc2-δ9 ura3-52 leu2-3 leu2-112 his4-519 | Schnappauf et al., 1997 |

TABLE 2

Plasmids used

| Plasmid | Description | Reference |
|---|---|---|
| pRS426 | 5726 bp shuttle vector, bla URA3 | Sikorski and Hieter, 1989 |
| pBluescript KS II | 2961 bp vector, bla, lacZ, Multiple Cloning Site (MCS) | Stratagene |
| pME1513 | p426MET25 with altered MCS (SacI pMET25 XbaI SpeI BamHI SalI SfiI NotI XhoI$^T$ CYCI KpnI) | Probst, 1998 |
| pME1524 | 5 kb Sau3A Fragment from H. p. in BamHI cleaved pRS426 | |
| pME1525 | 1.8 kb [ApaI/HindIII]-fragment from pME 1524 in pRS426 (SmaI) | |
| pME1526 | pBluescript II KS (ApaI/HindIII) + 1.8 kb (ApaI/HindIII)-fragment from pME1524 | |

TABLE 3

Oligonucleotides used

| Oligonucleotide | Size | Sequence |
|---|---|---|
| T3 | 20-mer | 5'-(AATTAACCCTCACTAAAGGG)-3' |
| T7 | 22-mer | 5'-(GTAATACGACTCACTATAGGGC)-3' |
| OLSK34 | 26-mer | 5'-(ATATAGATCTACAAA_AACTAAACAGG)-3' |
| OLSK35 | 28-mer | 5'-(ATATAGATCTGATGCG-ACGCAGAAAAGC)-3' |

2. Methods 2.1 Culturing of the Microorganisms 2.1.1 *Escherichia coli*

The cells were cultured in Luria-Bertani medium (LB: 1% tryptone, 0.5% yeast extract, 1% NaCl) at 37° C. For strains with the ampicillin resistance marker, 50 mg/l ampicillin were added to the medium.

2.1.2 *Hansenula polymorpha*

The cells were cultured at 37° C. either in "yeast extract peptone dextrose medium" (YEPD: 2% peptone, 1% yeast extract, 2% glucose) or in "yeast-nitrogen-base medium" (YNB: 0.15% yeast nitrogen base, 0.5% $(NH_4)_2SO_4$, 0.1% myo-inositol (200 mM), 5% glucose, supplemented with uracil for the present strain). All media were autoclaved before use and for solid media 2% agar was added.

2.1.3 *Saccharomyces cerevisiae*

The cells were cultured at 30° C. either in "yeast extract peptone dextrose medium" (YEPD: 2% peptone, 1% yeast extract, 2% glucose) or in "minimal vitamins medium" (MV: 0.15% yeast nitrogen base, 0.52% ammonium sulphate, 2% glucose, 1% succinate, 0.3% KOH). Supplements such as L-amino acids or uracil were added after Sherman et al. (1986) and, like the antibiotics, sterile filtered or autoclaved and added to the sterile medium. For solid media, 2% agar was added. The growth of the yeast cells was followed by measurement of the optical density at 600 nm.

2.2 Isolation of Nucleic Acids 2.2.1 Qiagen Plasmid DNA Preparation from *Escherichia coli*

Firstly the cultured bacteria were centrifuged off and the sediment formed was resuspended in 0.3 ml of buffer P1 (buffer description as per manufacturer). Then 0.3 ml of buffer P2 were added and the mixture incubated for 5 mins at room temperature. In the next step, 0.3 ml of the cooled buffer P3 were added and again incubated for 5 mins, this time on ice. Next, the mixture was centrifuged for 10 mins (12,000 rpm) and the supernatant added to a Quiagen-tip 20 column previously equilibrated with buffer QBT. After the supernatant had passed through the column, this was washed four times with 1 ml portions of buffer QC. The bound DNA was eluted with 0.8 ml of buffer QF. The eluted DNA was precipitated with 0.7 volumes of isopropanol and centrifuged off (30 min, 10,000 rpm). Finally the DNA was washed with 1 ml of 70% ethanol, dried and taken up in $H_2O$.

2.2.2 Isolation of Plasmid DNA from *Escherichia coli* (Birnboim and Doly, 1979)

The *E. coli* cultures were cultured overnight in 5 ml of LB-Amp at 37° C. on a rotary shaker. 1.5 ml of the culture were centrifuged off in an Eppendorf reaction vessel and the cells resuspended in 100 µl of solution I (50 mM glucose, 10 mM EDTA, 20 mM Tris-HCl, pH 8.4, 4 mg/ml lysozyme). After 7 mins incubation at RT, 200 µl of solution II (0.2 mM NaOH, 1% w/v SDS) were added, the mixture gently shaken and incubated for 5 mins on ice. 50 µl of solution III (3 M Na acetate, pH 4.8) were added, the mixture again gently shaken and incubated a further 7 mins on ice. The cell debris was centrifuged off and the supernatant extracted with 450 µl of $CH_2Cl_2$-saturated phenol in TE buffer (10 MM Tris-HCl, 1 mM EDTA, pH 8.0) and then with 450 µl of $CH_2Cl_2$. The plasmid was precipitated by addition of 1 ml of cold EtOH and incubation at −20° C. After 30 mins centrifugation at 4° C., the precipitate was washed with 200 µl of 70% EtOH, dried in vacuo and taken up in 50 µl of TE buffer (incl. 25 µg/ml RNase A). To dissolve the DNA this was heated for 5 mins at 65° C., and RNA degradation was effected using the heat-stable RNase A by incubation for 20 mins at 37° C. The plasmid DNA solution was stored at −20° C.

2.2.3 Isolation of Chromosomal DNA from *Hansenula polymorpha* (Hofman and Winston, 1987)

10 ml of YEPD medium were inoculated and incubated for about 15 hrs at 37° C. The cells were centrifuged off, resuspended in 0.5 ml of distilled water and again centrifuged off. The supernatant was discarded and 0.2 ml of lysis buffer (2% Triton X-100, 1% SDS, 100 mM NaCl, 10 mM Tris, pH 8.0, 1 mM EDTA), 0.2 ml of phenol/MeCl$_2$/TE and 0.3 g of glass spheres were added. To disintegrate the cells this was shaken for 3–4 mins and then the cell debris was centrifuged off (5 min, 13,000 rpm). The aqueous phase was placed in a new container and after addition of 1 ml of ethanol the DNA was precipitated and again centrifuged off. The sediment was resuspended in 0.4 ml of TE (10 mM Tris-HCl, 1 mM EDTA, pH 8.0) and 3 µl of RNase A (10 mg/ml) were added, whereupon the mixture was incubated for 5 mins at 37° C. Now 10 µl of 4M ammonium acetate and 1 ml of ethanol were added, the precipitated DNA was centrifuged off, the supernatant discarded, dried and taken up in 50 µl TE [sic].

2.3 Cloning Techniques 2.3.1 Polymerase Chain Reaction ('PCR'; Saiki et al., 1985)

Polymerase chain reactions were performed with the heat-stable enzyme Taq-polymerase (Fermentas) in Gene-AmpTM reaction vessel (Eppendorf). Usually each time 5–50 nmol of primer oligonucleotide and 10–100 ng of DNA as matrix were used in 20–50 µl of reaction buffer in accordance with the manufacturer's instructions. As a rule, 30 cycles of the following temperature regime were performed: 30 secs denaturation at 94° C. 30 secs hybridisation at specific reaction temperature/30 secs-3 mins synthesis at 72° C. for Taq-DNA polymerase. The PCR cycles were initiated by a 3 minute denaturation step and finished by a final synthesis step of 5 mins.

2.3.2 DNA Restriction

For analytical restriction reactions, ca. 0.5 µg of DNA were incubated with 1–2 units of restriction enzyme in a volume of 20 µl for 2–3 hrs at 37° C. For the restriction of preparative quantities of DNA, correspondingly larger volumes and quantities of enzyme were used. Reaction buffers were used in accordance with the manufacturer's instructions.

2.3.3 Agarose Gel Electrophoresis 0.1 vol. of DNA dye (25% w/v Ficoll 400, 0.25% w/v Bromphenol blue, 0.25% w/v xylenecyanol, 200 mM EDTA, pH 8.0) were added to the restriction mixture, and the DNA fragments were separated electrophoretically in a horizontal agarose gel in TAE buffer (40 mM Tris acetate, 20 mM NaOAc, 2 mM EDTA, pH 8.3) in the presence of 0.5 µg/ml ethidium bromide. DNA bands were detected with a UV Transilluminator (254 mm).

2.3.4 Isolation of DNA Fragments from Agarose

To isolate DNA fragments from the agarose gel, the columns and buffers of the QIAquick Gel Extraction Kit Protocol were used in accordance with the manufacturer's use directions. For this, the DNA fragments were firstly cut out from the gel and weighed. 3 volumes of the buffer QX1 were added, and incubated for 10 mins at 50° C. As soon as the gel fragment had completely dissolved, 1 volume of isopropanol was added and the mixture was placed on the QIAquick column and centrifuged off. To wash the DNA bound onto the column, 0.75 ml of PE buffer were added and again centrifuged. Finally, the DNA was eluted with 50 µl of H$_2$O.

2.3.5 Ligation of DNA Fragments (Maniatis et al., 1989)

Linear DNA fragments with sticky or smooth ends were ligated in a reaction mixture in a total volume of 20 µl with ligation buffer (20 mM Tris-HCl, 10 mM MgCl$_2$, 10 mM DTT, 0.6 mM ATP, pH 7.6) and 5 units of T4-DNA ligase overnight at 15° C. or for 5 hrs at room temperature. The concentration of DNA was between 1 and 10 µg/ml, and the vector/insert DNA mole ratio between 1:5 and 1:10. Following the ligation reaction, the DNA was used for transformation without further purification.

2.4 Transformation Methods 2.4.1 Transformation of E. coli (Inoue et al., 1990)

Cells of a 250 ml SOB culture (2% tryptone, 0.5% yeast extract, 10 mM NaCl, 2.5 mM KCl, 10 mM MgCl$_2$, 10 mM MgSO$_4$) in the exponential phase were centrifuged off for 10 mins at 4° C. (1000×g) and resuspended in 80 ml of TB buffer (10 mM PIPES, 15 mM CaCl$_2$×H$_2$O, 250 mM KCl, pH 6.7, 55 mM MnCl$_2$×H$_{20}$O). After incubation (10 mins on ice), the cells were again centrifuged off at 4° C. and 2,500 rpm. Then the sediment was carefully resuspended in 20 ml of TB buffer and also carefully mixed thoroughly with 7% DMSO. After 10 min incubation on ice, the now competent cells were aliquotted, shock-frozen in liquid N$_2$ and stored at −70° C. 200 µl of competent cells were added to 1–10 µg of DNA and incubated on ice for 30 mins. After 30 secs heat shock at 42° C., the mixture was chilled on ice, treated with 800 µl of SOC medium (SOB, incl. 20 mM glucose) and shaken for 1 hr at 37° C. Various amounts (10–900 µl) of the cell culture were plated out on solid selective medium (agar plates with LB complete medium, supplemented with 50 µg/ml ampicillin) and finally the plates incubated overnight at 37° C. to give transformed cells time for colony formation.

2.4.2 S. cerevisiae Transformation (modified after Ito et al, 1983)

0.5 ml of a fresh yeast culture, grown overnight, were used per transformation mix. The cells were centrifuged off at room temperature (5 mins, 3,500 rpm) and the supernatant was removed. Now the transforming DNA and 50 µg of carrier DNA were added and mixed. Finally, 0.5 ml of PEG (40% PEG3350, 0.1M LiOAc, 10 mM Tris pH 7.5, 1 mM EDTA, 0.1 M DTT) were added, and the transformation mixes were shaken and incubated for at least 12 hrs at room temperature. After a 20 min heat shock (42° C.), the cells were carefully centrifuged, and incubated in 1 ml YEPD for 1 hr at 30° C. Finally the cells were centrifuged for 5 secs in the bench centrifuge, resuspended in the remaining liquid after discarding of the supernatant and plated out on selection media.

2.5 Hybridisation Techniques 2.5.1 Southern Hybridisation (Southern, 1975)

For the Southern hybridisation, ca. 10 µg of chromosomal DNA were dissolved in TE buffer (10 mM Tris-HCl, 1 mM EDTA, pH 8.5) and subjected to restriction digestion for 12 hrs with a suitable restriction enzyme. The cleaved DNA was separated in a 1% agarose gel. The agarose gel was washed 3 times, for 20 mins each time, firstly in 0.25M HCl, then in 5M NaOH/1.0M NaCl and finally in 1M NH$_4$OAc. Now the separated DNA was transferred by 12-hour dry-blotting onto a nitrocellulose membrane. This was next washed for 2 mins in 2×SSC (0.1M NaCl, 10 mM NaOAc, pH 7.0), dried in air, and finally "crosslinking" was performed for 5 mins under UV light (254 nm).

The membrane was prehybridised for 30 mins at 65° C. with 50 ml of Church buffer (7% SDS, 1% BSA, 1 mM EDTA, 250 mM Na phosphate, pH 7.2), after which half of the hybridisation solution was discarded. Now the radioactively-labelled DNA probe was added and the hybridisation was performed overnight at 65° C. Following the hybridisation, the membrane was washed for 30 mins at 65° C. with 2×SSC/0.1% SDS and then exposed on an Xray film or on a phosphor imaging plate.

2.5.2 Preparation of the Probe DNA

For the preparation of the probe DNA, the Prime-It (Random Primer Labeling Kit) from the firm Stratagene was used in accordance with the manufacturer's instructions. The DNA required was previously amplified by PCR and then used for the probe preparation.

2.6 Characterisation of the Chorismate Mutase from *Hansenula polymorpha*

2.6.1 Crude Extract Preparation

The yeast cells were cultured in YNB medium, individually supplemented for the particular yeast strains, and harvested at an $OD_{546}$ of ca. 4. Crude extracts were prepared as described by Kradolfer et al. (1977), using an Amicon French Press.

2.6.2 Determination of Protein Content

The protein content of the protein solutions was determined by the method of Bradford (1976) with BSA as protein standard.

2.6.3 Measurement of Enzyme Activity

For the measurement of the chorismate mutase activity, stop tests, such as those developed by Schmidheini et al. (1989), with a few modifications were performed. All enzyme tests and extinction measurements were performed at 30° C. The 500 µl reaction mixes contained 50 mM potassium phosphate buffer, pH 7.6, 2 mM EDTA, 20 mM DTT and 10 µl of the protein fraction concerned. The reaction, i.e. the conversion of chorismate to prephenate, was started by addition of chorismate at a final concentration of 1 mM and stopped after 10 mins with 500 µl of 1M HCl, which also effects the conversion of prephenate into phenylpyruvate which is measurable at $OD_{320}$.

Neutralisation by addition of 4 ml of 1M NaOH ended the reaction. The measurement of the $OD_{320}$ was performed against $H_2O$, and similar solutions without enzyme were used as null values. The measurements were also performed in the presence of 5 µM L-tryptophan. The null values of the measurements without enzyme were subtracted from the absorption values. With the molecular extinction coefficient of phenylpyruvate at 30° C. of 13095 µl/(mol×cm), the conversion rate (µmol product/(min×mg protein)) and hence the specific activity (conversion/mg protein) could be calculated.

Results

1. Preparation of a Genomic Gene Bank from *Hansenula polymorpha*

Figure 1:
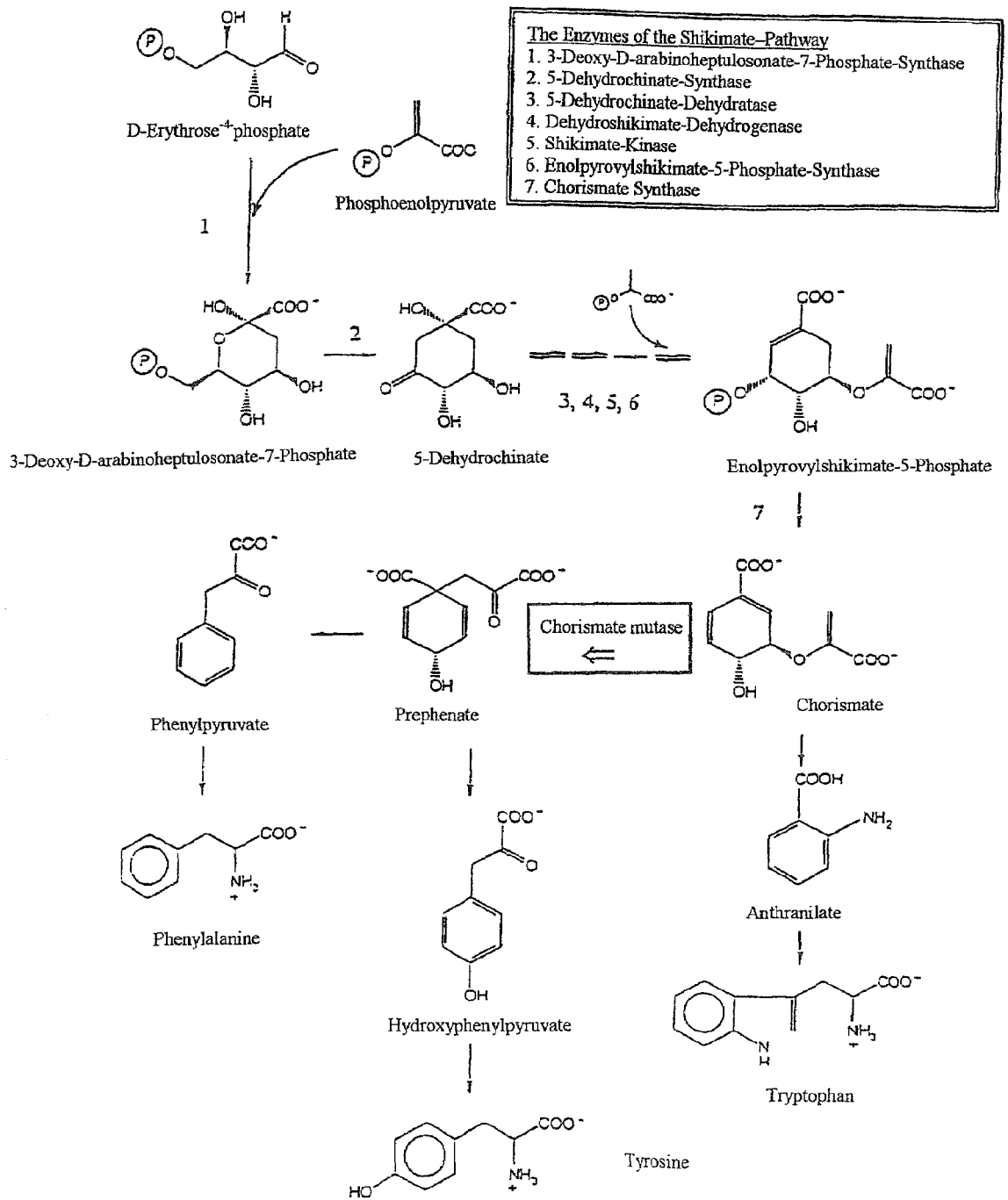
FIG. 1 shows the biosynthesis of the aromatic amino acids via the shikimate pathway.
Figure 2:
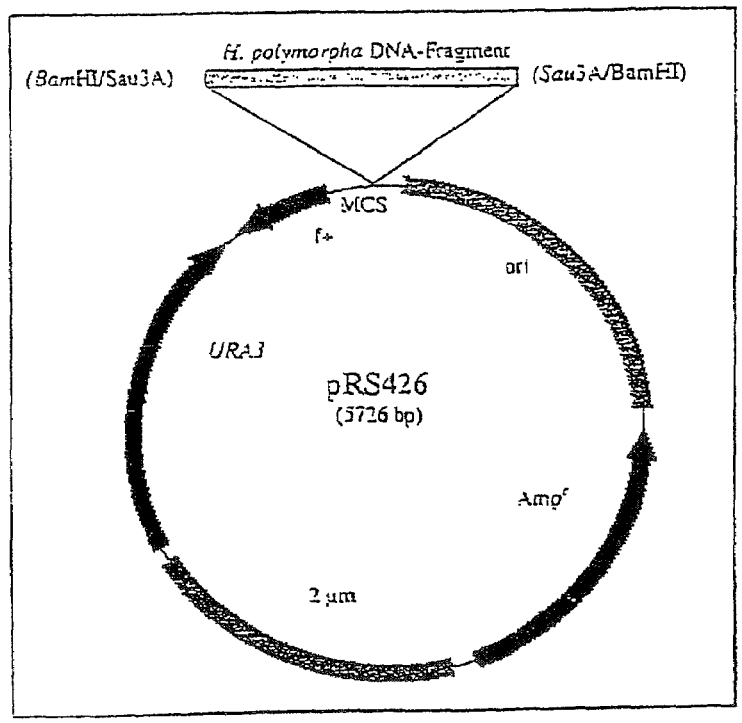
FIG. 2 shows the ligation of the DNA fragments into the vector pRS426. The vector was linearised with the restriction enzyme BamHI and the genomic Sau3A DNA fragments from H. polymorpha were ligated into this cleavage site. This is possible, since the cleavage sites BamHI and Sau3A are compatible.

For the preparation of a genomic gene bank, chromosomal DNA from *Hansenula polymorpha* RB11 was isolated and this was subjected to partial restriction with the enzyme Sau3A The recognition sequence of this enzyme is relatively frequently present in the genome, since it consists of only 4 bases. During the 5-hour reaction time, aliquots were taken at 15 min intervals, and the reaction in each stopped by addition of EDTA. In this way, it was ensured that the chromosomal DNA was cleaved into fragments of different size. The cleaved DNA was separated in an agarose gel, divided into different size fractions between 1 kb and 10 kb, and correspondingly extracted from the gel. The extracted fragment fractions were ligated into the vector pRS426 (Sikorski and Hieter, 1989), previously linearised with BamHI (FIG. 2).

The plasmid library thus obtained was transformed into *E. coli*, during which the antibiotic resistance encoded by the bla-gene was selected for in the presence of ampicillin. Overall, about 150,000 transformants were obtained. These were washed from the plates with LB medium and stored at −20° C. after addition of glycerine.

2. A Genomic 1.8 kb DNA Fragment from *H. polymorpha* Complements the aro7Δ-Phenotype in *S. cerevisiae*

Figure 3:
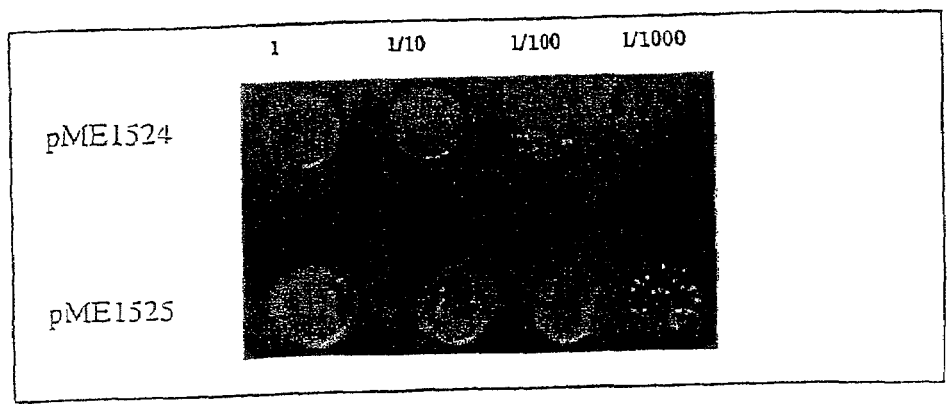
FIG. 3 shows the growth comparison of cells transformed with 2 complementing DNA fragments. To highlight the different growth rates, cell material of the cells complemented with a 5 kb (pME1524) or a 1.8 kb (pME1525 subclone of pME1524) DNA fragment was diluted in water and 20 µl of each dilution stage was applied onto minimal medium. The optical density of the different dilution stages is the same in each case, however since only the fundamentally different growth rates had to be illustrated, no accurate growth parameters were determined.

The plasmids of the genomic *H. polymorpha* bank were isolated from *E. coli* and transformed into the *S. cerevisiae* strain RH2185 (MATα(Δaro7::LEU2 suc2-δ9 ura3–52 leu2–3 lue2–112 his4–519), in order to complement its Tyr/Phe auxotrophy, which is attributable to a deletion in the ARO7 gene. The transformed yeast cells were firstly selected for uracil prototrophy and thus for the presence of the URA3 gene of the vector pRS426 (SC-Ura) and then transferred to minimal medium (YNB+Trp+His). After about 5 incubation stages at 30° C., 3 transformed yeast colonies were isolated which were capable of growing in the absence of uracil, tyrosine and phenylalanine. The plasmids were isolated and even after a retransformation were capable of complementing the ARO7 deletion in RH2185. By restriction analysis, an approximately 5 kb additional DNA fragment was identified in the vector pRS426. For further localisation of the DNA fragment, a subcloning was performed wherein the fragments obtained were again ligated into the vector pRS426. These different plasmids were now, analogously to the plasmids of the genomic bank, examined for their ability to complement the Tyr/Phe auxotrophy in RH2185. An approximately 1.8 kb ApaI/XbaI fragment was thus obtained, which was capable of doing this. This finding was confirmed by repeated retransformation. It was striking that the 1.8 kb *H. polymorpha* DNA fragment (in the plasmid pME1525) in transformed yeast cells showed growth comparable with the wild type, while the 5 kb *H. polymorpha* fragment (in the plasmid pME 1524) in transformed yeast cells resulted in markedly slower growth (FIG. 3).

Figure 4:
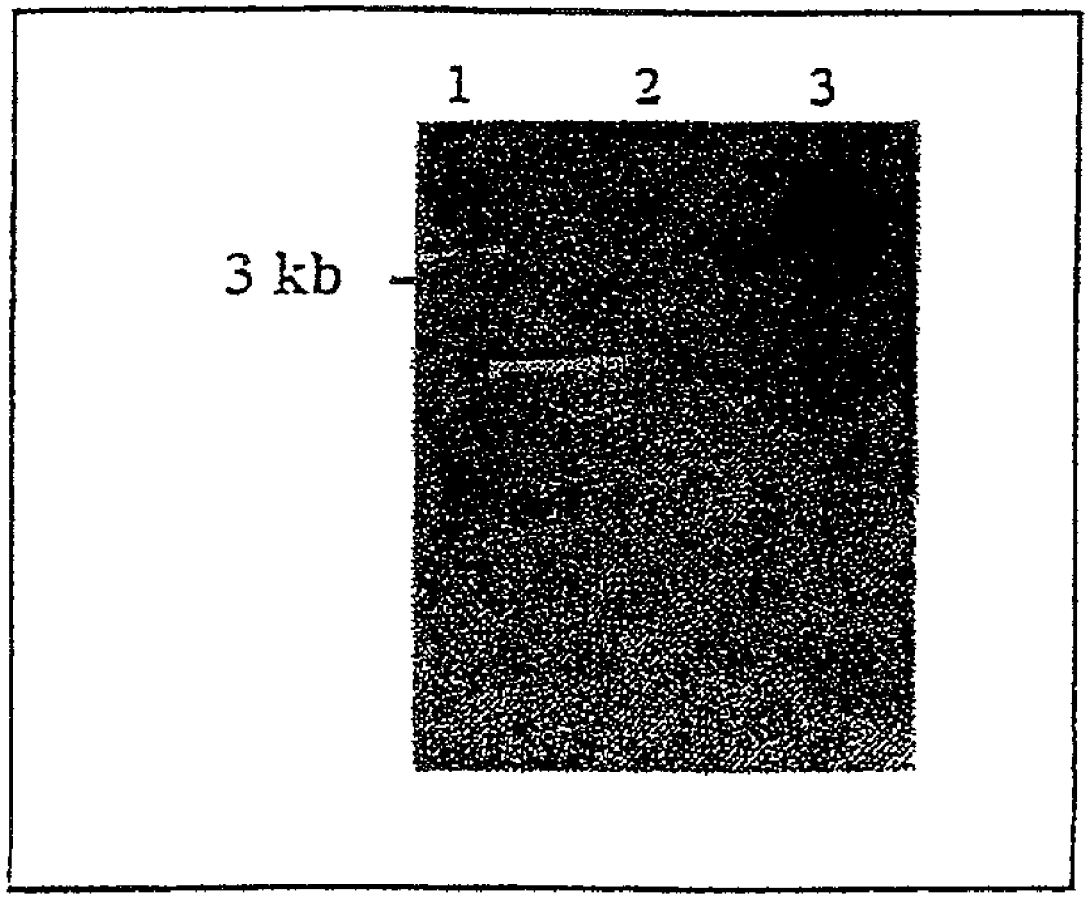
FIG. 4 shows the autoradiograph of a hybridisation of chromosomal DNA from different fungi with a 1.8 kb DNA fragment from H. polymorpha, which is capable of complementing the phenylalanine/tyrosine auxotrophy of the S. cerevisiae aro7Δ selection strain. Chromosomal DNA from S. cerevisiae (1), A. nidulans (2) and H. polymorpha (3) was cleaved with the restriction enzyme EcoRV and hybridised with a $^{32}P$ radioactively labelled DNA probe, prepared using the genomic 1.8 kb DNA fragment from H. polymorpha.

In order to confirm that the complementing 1.8 kb fragment originated from *Hansenula polymorpha*, this was used as the probe in a Southern hybridisation. The chromosomal DNA from *H. polymorpha, A. nidulans* and *S. cerevisiae* was cleaved with the restriction enzyme EcoRV and after hybridisation with the probe a clear signal could be seen with *H. polymorpha*, a weak signal with *S. cerevisiae* and no signal with *A. nidulans*. Furthermore, it could be shown by the Southern hybridisation that the gene occurs only once in the genome of *H. polymorpha* (FIG. 4).

The 1.8 kb DNA fragment from *H. polymorpha* RB11 was sequenced completely and an open reading frame consisting of 843 bp could be identified (FIG. 5), which showed a 58% agreement with the ARO7 gene from *S. cerevisiae*. It can thus be assumed that this is the gene of the yeast *Hansenula polymorpha* homologous to ARO7, which is referred to below as HARO7.

3 Preparation of Various Deletion Constructs

On the basis of the sequence of the 1.8 kb DNA fragment from *H. polymorpha*, the primers OLSK34 and OLSK35 were used for the preparation of various haro7Δ-deletion constructs. The various deletion constructs were transformed into *H. polymorpha*, in order to confirm the identity of the gene and to confirm that that no isoenzymes of chorismate mutase exist in *H. polymorpha*.

Figure 6:
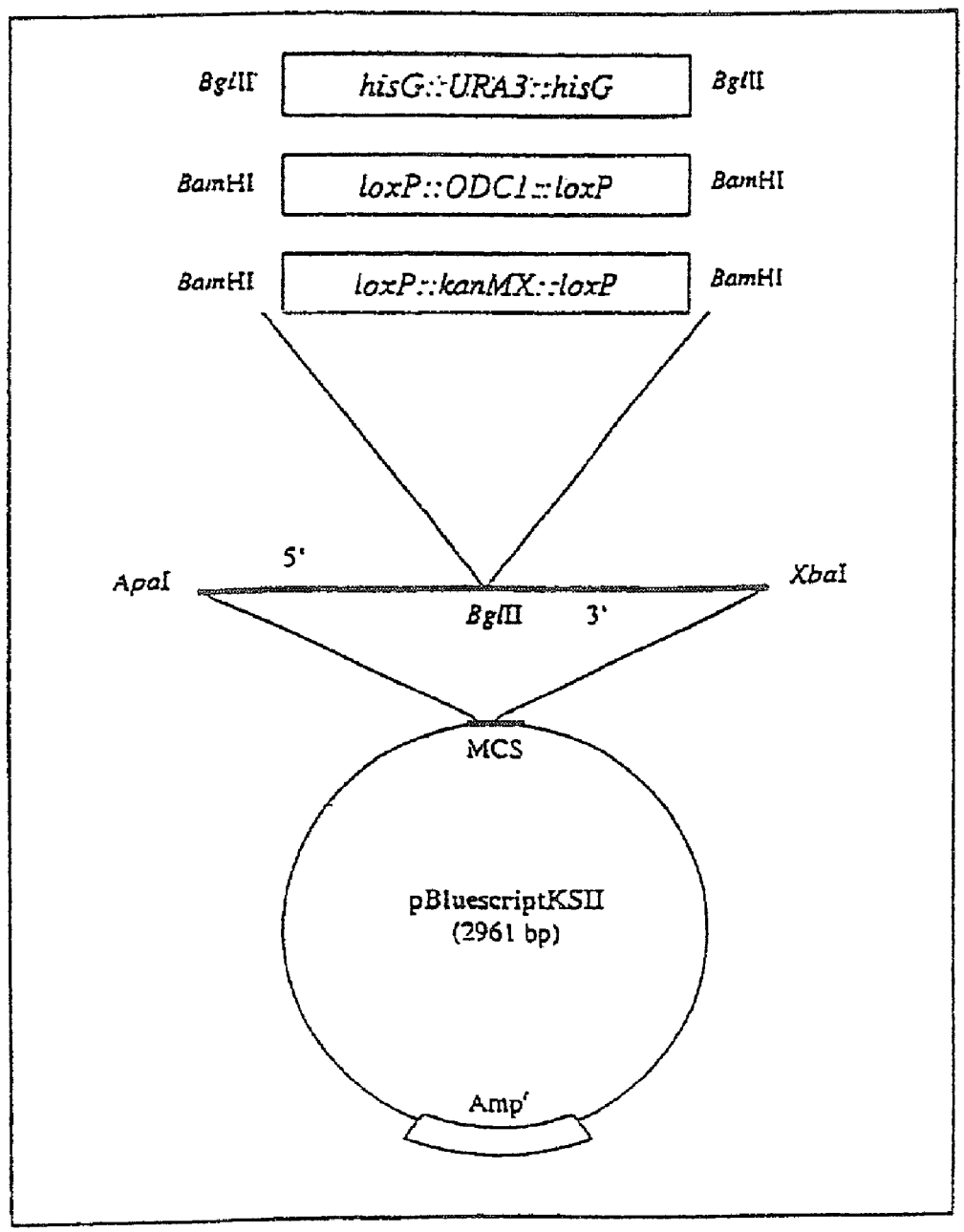
FIG. 6 shows the amplification of the flanking regions of the HARO7-ORF. The flanking regions of the HARO7 gene were amplified with the primers OLSK34/T7 and OLSK35/T3 respectively and then cleaved with ApaI/BglII and BglII/XbaI respectively.

By deletion of HARO7 in *Hansenula polymorpha*, the identity of this gene can be conclusively proved and the existence of alternative genes checked. At the same time, the construction of such a deletion mutant opens up new selection possibilities. For the preparation of a haro7Δ deletion strain, three different disruption cassettes were constructed. For the necessary integration into the *Hansenula polymorpha* genome, the flanking regions of the HARO7 gene, which should effect the deletion of the HARO7 gene by homologous recombination, were used for all three constructs. The flanking region in the 3' direction was amplified using the primers OLSK34 and T7, and next cleaved with the restriction enzymes ApaI and BglII. The flanking region in the 5' direction was amplified using the primers OLSK35 and T3, and cleaved with the restriction enzymes XbaI and BglII. This is possible as the primers OLSK34 and OLSK35 contain a BglII cleavage site (FIG. 6).

Both fragments were ligated into the ApaI/XbaI cleaved vector pBluescript KSII and then the vector was again opened with BglII, in order to introduce various disruption cassettes (FIG. 7).

The hisG::URA3::hisG disruption cassette (Schneider et al., 1996) was cleaved with BglII and ligated into the vector described above. By means of the UTRA3 marker, integration of the cassette into the genome of H. polymorpha can be checked. Whether a homologous integration, i.e. a deletion of HARO7, has in fact taken place can be shown by selection for phenylalanine/tyrosine auxotrophy and by Southern hybridisation. The hisG components favour the conclusive excision of the URA3 marker, which can be checked by counter-selection with 5-FOA (5-fluoroorotic acid), since the URA3 gene product causes a toxic conversion of 5-FOA so that only cells without the URA3 marker are capable of surviving (Boeke et al., 1984).

The loxP::kanMX::loxP disruption cassette (Güldener et al., 1996) was cleaved with BamHI and ligated into the vector described above. By means of the kanMX marker, integration of the cassette into the genome of Hansenula polymorpha can be checked by selection for kanamycin resistance (G418). The $kan^r$ gene is flanked by the translation elongation factor (TEF) promoter and terminator (Steiner and Philippsen, 1994) of the filamentous fungus Ashbya gossypii. Whether a homologous integration has in fact taken place can be shown by selection for phenylalanine/tyrosine auxotrophy and by Southern hybridisation. In this system, the possibility exists of removing the marker again from the genome after the deletion has taken place. This occurs through the Cre-loxP recombination system of the bacteriophage P1 (Güldener et al., 1996). The plasmid pSH47 (Austin et al., 1981) contains the Cre recombinase gene with a GAL1 promoter connected upstream and in addition the components ARS, CEN and a URA3 marker. Galactose induces the expression of the recombinase and this effects the removal of the marker from the genome by recombination of the flanking loxP regions.

The loxP::ODC1::loxP disruption cassette is analogous to the loxP::kanMX::loxP disruption cassette (Güldener et al., 1996), except that the kanMX gene has been replaced by the ODC1 gene (=URA3) from Hansenula polymorpha (M Hiller, personal communication). In this case also, the possibility exists of removing the marker again from the genome after the deletion has taken place. The removal of the marker can in this case be checked by selection on 5-fluoroorotic acid (5-FOA) medium, since the ODC1 gene product causes a toxic conversion of 5-FOA so that only cells without the ODC1 marker are capable of surviving (Boeke et al., 1984).

The transformation of the hisG::URA3::hisG disruption cassette into H. polymorpha RB11 resulted in a mutant which had a tyrosine/phenylalanine auxotrophy and a uracil prototrophy, and thus possessed the phenotype to be expected.

4. Example of Recombinant Expression of Proteins Using Auxotrophic Yeast Strains and Functional Complementation for Plasmid Selection:

For the expression of a recombinant protein in H. polymorpha using a nucleic acid molecule according to the invention, suitable expression plasmids can be prepared. For example, the plasmid pFPMT121 from the firm Rhein Biotech GmbH serves as the basis for this. This bears the URA3 gene from S. cerevisiae for selection in H. polymorpha after transformation of uracil-auxotrophic strains such as e.g. RB11 (Weydemann et al., 1995) (odc1 or ura3). The FMD promoter (EP-B-O 299 108) from H. polymorpha, followed by the MOX terminator sequence (Godecke et al, 1994), serves as the expression module.

After digestion with the restriction enzyme NdeI, a 5 kb DNA fragment can be isolated from pFPMT121. This corresponds to the plasmid without the URA3-coding sequence. After filling of the overhangs of this DNA fragment by Klenow treatment, this can be ligated with a 1.3 kb Eco72I/SspI fragment from pSK69 (SEQ ID NO:3). The resulting plasmid now bears as a selectable marker gene the chorismate mutase gene (HARO7) from H. polymorpha, which codes for the enzyme chorismate mutase. The selection is performed for prototrophy with respect to tyrosine and phenylalanine.

Alternatively, the 1.3 kb Eco72I/SspI fragment can be cloned into the plasmid pFPMT121 linearised with SmaI. This procedure results in an expression plasmid which bears two marker genes, URA3 and HARO7.

A recombinant DNA fragment for the expression of a heterologous protein can now be cloned into these plasmids into a suitable restriction cleavage site directly behind the FMD promoter region. Here, the coding DNA sequence is preferably fused with a DNA sequence which guarantees the secretion and processing of the expression product in H. polymorpha. As an example of such a control sequence, the MFal gene from S. cerevisiae (Arnold et al, 1998) may be mentioned.

Transformed to the heterologous expression plasmids and positive transformants selected by growth on minimal medium.[sic] By alternate growth in minimal medium and complete medium, after many generations it is possible to identify from these ones in which the expression construct has been mitotically stably integrated into the genome. Then that strain in which the expression module is present in highest copy number within the host genome is preferably used as the expression strain. The expression of the heterologous protein preferably takes place after culturing of the strain in glucose-containing medium, by changing to medium with glycerine as the only C source. Under these conditions, there is derepression of the FMD promoter, linked with strong expression of the heterologous protein. Finally, this can be isolated in pure form from the purified culture supernatant by standard chromatographic methods.

5. The 1.8 kb Fragment from Hansenula polymorpha Codes for a Protein with Chorismate Mutase Activity To check whether the 1.8 kb fragment contains a gene which codes for a protein with chorismate mutase activity, cell extracts of different plasmid-bearing yeast strains were prepared using a French Press and their chorismate mutase activities were measured. For the measurement of the specific enzyme activity, cell extracts from S. cerevisiae RH2185 pRS426), H. polymorpha RB11, S. cerevisiae RH2185(pME1524) and S. cerevisiae RH2185(pME1525) were prepared. It could be shown that both the 5 kb fragment (pME1524) and also the 1.8 kb fragment (pME1525) from H. polymorpha code for genes for a chorismate mutase activity (table 4).

TABLE 4

Specific chorismate mutase activities (U/mg protein) of various cell extracts.

| | Specific Activity (U/mg) | |
|---|---|---|
| | (−tryptophan) | (+tryptophan) |
| S. cerevisiae-RH2185 + pRS426 | 0 | 0 |
| H. polymorpha-RB11 | 0.379 | 0.349 |
| S. cerevisiae-RH2185 + pME1524 | 0.191 | 0.127 |
| S. cerevisiae-RH2185 + pME1525 | 0.469 | 0.263 |

The table shows the mean value of 4 activity measurements in each case. The values for cell extracts from S. cerevisiae RH2185 + pRS426, S. c. + pME1524, S. c + pME1525 and H. polymorpha RB11 were measured. The measurements were in each case performed with and without 500 μM tryptophan.

6. Identification of the HARO7 Gene of the Yeast *Hansenula polymorpha*

The complementing 1.8 kb DNA fragment was completely sequenced using a T3 and a T7 primer (FIG. 5).

The enzyme chorismate mutase is encoded in the yeast *Hansenula polymorpha* by a gene which consists of 843 bp and has been named HARO7. This gene was cloned by complementing the phenylalanine/tyrosine auxotrophy of a *Saccharomyces cerevisiae* aro7Δ deletion strain with a genomic gene bank from *Hansenula polymorpha*. Hence the *H. polymorpha* promoter is functional in *S. cerevisiae*. No introns are present, and a 32 kDA protein consisting of 280 amino acids can be derived from the sequence. The amino acid sequence of the chorismate mutase from *Hansenula polymorpha* shows 58% identity to that from *Saccharomyces cerevisiae* and 44% to that from *Aspergillus nidulans*. A striking feature in the comparison of these amino acid sequences is an endpiece consisting of 23 amino acids in the sequence from *H. polymorpha*, which is present neither in *S. cerevisiae* nor in *A. nidulans*, nor in other eukaryotic chorismate mutase amino acid sequences.

LITERATURE

Agaphonov, M. O., Poznyakovski, A. I., Bogdanova, A. I., and Ter-Avanesyan, M. D. (1994) Isolation and characterisation of the LEU2 gene of *Hansenula polymorpha*. Yeast 10, 509–513.

Arnold, C. E., Parelsh, R. N., Yang, W. and Wittrup, K. D. (1998) Leader peptide efficiency correlates with signal recognition partide dependence in *Saccharomyces cerevisiae*. Biotechnol. Bioeng. 59, 286–293.

Austin, S., Ziese, M., and Sternberg, N. (1981) A novel role for site-specific recombination in maintenance of bacterial replicons. *Cell* 25, 729–736.

Birnboim H. C. and Doly, J. (1979) A rapid alkaline extraction procedure for screening recombinant plasmid DNA. Nucl. Acids Res. 7, 1513–1523.

Boeke, J. D., Lacroute, F., and Fink, G. R. (1984) A positive selection of mutants lacking orotidine-5'-phosphate decarboxylase activity in yeast: 5-fluoro-orotic acid resistance. Mol. Gen. Genet. 197, 345–346.

Bradford, M. M. (1976) A rapid and sensitive method for the quantitation of microgram quantities of protein utilizing the principle of protein-dye binding. Anal. Biochem. 72, 248–254.

Braus, G. H. (1991) Aromatic amino acid biosynthesis in the yeast *Saccharomyces cerevisiae:* a model system for the regulation of an eukaryotic biosynthetic pathway. Microbiol. Rev. 55. 349–370.

Buckholtz, R. G. and Gleeson, M. A. G. (1991) Yeast systems for the commercial production of heterologous proteins. Biotechnology 9, 1067–1072.

Dobson, M. J., Tuite, M. F., Roberts, N. A., Kingsman, A. J., Kingsman, S. M., Perkins, R. E., Conroy, S. C., and Fothergill, L. A. (1982) Conservation of high efficiency promoter sequences in *Saccharomyces cerevisiae*. Nucl. Acids Res. 10, 2625–2637.

Dohmen, R. J., Strasser, A. W. M., Dahlems, U., and Hollenberg, C. P. (1990) Cloning of the *Schwanniomyces occidentales* glucoamylase gene (GAM1) and its expression in *Saccharomyces cerevisiae*. Gene 95, 111–121.

Gellissen, G., Hollenberg, C. P., and Janowicz, Z. A. (1994) Gene expression in methylotrophic yeasts. In: Smith, A. (ed.) Gene expression in recombinant microorganisms. Marcel Dekker, New York, 195–239.

Gellissen, G. and Hollenberg, C. P. (1997) Applications of yeasts in gene expression studies: a comparison of *Saccharomyces cerevisiae, Hansenula polymorpha* and *Kluyveromyces lactis*—a review. Gene 190, 87–97.

Gilbert, S. C., Van Urk, H., Greenfield, D. M., McAvoy, M. J., Denton, K. A., Coghlan, D., Jones, G. D., and Mead, D. J. (1994) Increase in copy number of an integrated vector during continuous culture of *Hansenula polymorpha* expressing functional human haemoglobin. Yeast 10, 1569–1580.

Godecke, S., Eckart, M., Janowicz, Z. A., and Hollenberg, C. P. (1994) Identification of sequences responsible for transcriptional regulation of the strongly expressed methanol oxidase-encoding gene in *Hansenula polymorpha*. Gene 139, 35–42.

Güldener, U., Heck, S., Fiedler, T., Beinhauer, J., and Hegemann, J. H. (1996) A new efficient gene disruption cassette for repeated use in budding yeast. Nucl. Acids Res. 24, 2519–2524.

Hansen, H. and Hollenberg, C. P. (1996) History of *Hansenula polymorpha* Research. In: Nonconventional Yeasts in Biotechnology. A Handbook. Klaus Wolf (ed.). Springer-Verlag Berlin, Heidelberg, New York.

Hoffman, C. S. and Winston, F. (1987) A ten-minute DNA preparation from yeast efficiently releases autonomous plasmids for transformation of *Escherichia coli*. Gene 57, 267–272.

Inoue, H., Nojima, H., and Okayama, H. (1990) High efficiency transformation of *Escherichia coli* with plasmids. Gene 96, 23–28.

Ito, H., Jukuda, Y., Murata, K., and Kimura, A. (1983) Transformation of intact yeast cells treated with alkali cations. J. Bacteriol. 153, 163–168.

Janowicz, Z. A., Eckart, M. R., Drewke, C., Roggenkamp, R. O., and Hollenberg, C. P. (1985) Cloning and characterisation of the DAS gene encoding the major methanol assimilatory enzyme from the methylotrophic yeast *Hansenula polymorpha*. Nucl. Acids Res. 13, 3043–3062.

Jensen, R. A. and Stenmark, S. L. ((1975) The ancient origin of a second microbial pathway for L-tyrosine biosynthesis in prokaryotes. J. Mol. Evol. 4, 249–259.

Kradolfer, P., Zeyer, J., Miozzari, G., and Hütter, R. (1977) Dominant regulatory mutants in chorismate mutase of *Saccharomyces cerevisiae*. FEMS Microbiol. Lett. 2, 211–216.

Ledeboer, A. M., Edens, L., Maat, J., Visser, C., Bos, J. W., Verrips, C. T., Janowicz, Z. A., Eckart, M., Roggenkamp, R., and Hollenberg, C. P. (1985) Molecular cloning and characterisation of a gene coding for methanol oxidase in *Hansenula polymorpha*. Nucl. Acids Res. 13, 3063–3082.

Lepetic, A., Seigelchifer, M., Arduino, R. C., Lazovski, J., Nacinivich, F., Sturba, E., and Stamboulian, D. (1996) Novel recombinant HB vaccine produced by a high-level expression *Hansenula polymorpha* yeast system. Clin. Infect. Dis. 23, 276.

Lodder, J. (1970) The yeast, a taxonomic study. North-Holland Publishing, Amsterdam.

Lorence, J. H. and Nester, E. W. (1967) Multiple molecular forms of chorismate mutase in *Bacillus subtilis*. Biochemistry 6, 1541–1552.

Maniatis, T., Fritsch, E. F., and Sambrook, J. (1989) Molecular Cloning, a laboratory manual. Book 1. 2nd edn., Cold Spring Harbor Laboratory Press, Cold Spring Harbor, N.Y.

Müller, S., Sandal, T., Kamp-Hansen, P., and Dalbge, H. (1998) Comparison of Expression Systems in the yeasts *Saccharomyces cerevisiae, Hansenula polymorpha, Kluyveromyces lactis, Schizosaccharomyces pombe* and *Yarrowia lipolytica*. Cloning of two novel promoters from *Yarrowia lipolytica*. Yeast, 14, 1267–1283.

Rave, N., Crkvenjaker, R., and Bödtker, H. (1979) Identification of procollagen mRNAs transferred to diazobenzyloxymethyl paper from formaldehyde agarose gels. Nucl. Acids Res. 6, 3559–3567.

Saiki, R. K., Schafr, S., Faloona, F., Mullis, K. B., Horn, G. T., Erlich, H. E., and Arnheim, N. (1985) Enzymatic amplification of (-globin genomic structures and restriction site analysis for diagnosis of sickle cell anaemia. Science 230, 1350–1354.

Schmidheini, T., Sperisen, P., Paravicini, G., Hütter, R., and Braus, G. H. (1989) A single point mutation results in a constitutively activated and feedback-resistant chorismate mutase of *Saccharomyces cerevisiae*. J. Bacteriol. 171, 1124–1153.

Schneider, B. L., Steiner, B., Seufert, W., and Futcher, A. B. (1996) pMPY-ZAP: A reusable Polymerase Chain Reaction-directed gene disruption cassette for *Saccharomyces cerevisiae*. Yeast 12, 129–134.

Sherman, F., Fink, G. R., and Hicks, J. B. (1986) Laboratory Course Manual for METHODS IN YEAST GENETICS. Cold Spring Harbor Laboratory, Cold Spring Harbor, N.Y.

Sikorski, R. S. and Hieter, P. (1989) A system of shuttle vectors and yeast host strains designed for efficient manipulation of DNA in *Saccharomyces cerevisiae*. Genetics 122, 19–27.

Southern, E. M. (1975) Detection of specific sequences among DNA fragments separated by gel electrophoreses. J. Mol. Biol. 98, 503–517.

Steiner, S. and Philippsen, P. (1994), Sequence and promoter analysis of the highly expressed TEF gene of the filamentous fungus *Ashbya gossypii*. Mol. Gen. Genet. 242, 263–271.

Van der Klei, I. J., Harder, W., and Veenhuis, M. (1991) Methanol metabolism in a peroxisome-deficient mutant of *Hansenula polymorpha:* a physiological study. Arch. Microbiol. 156, 15–23.

Verduyn, C., Postman, E., Scheffers, W. A., and Van Dijken, J. P. (1992) Effect of benzoic acid on metabolic fluxes in yeasts: a continuous-culture study on the regulation of respiration and alcoholic fermentation. Yeast 8, 501–517.

Weidemann, W., Gromoll, J., and Keller, R. (1989) Cloning and sequence analysis of cDNA for precursor of a crustacean hyperglycaemic hormone. FEBS Lett. 257, 31–34.

Weydemann, U., Keup, P., Piontek, M., Strasser, A. W. M., Schweden, J., Gellissen, G., and Janowicz, Z. A. (1995) High-level secretion of hirudin by *Hansenula polymorpha*—authetic processing of three different preprohirudins. Appl. Microbiol. Biotechnol. 44, 377–385.

Woodcock, D. M. (1989) Quantitative evaluation of *Escherichia coli* host strains for tolerance to cytosine methylation in plasmid and phage recombinants. Nucl. Acids Res. 17, 3469–3478.

---

The invention claimed is:

1. An isolated nucleic acid molecule, comprising a nucleic acid encoding a polypeptide with chorismate mutase activity or the complement thereof, wherein the nucleic acid is selected from
 (a) a nucleic acid comprising the DNA sequence set forth in SEQ ID NO: 1 or the RNA sequence corresponding thereto; and
 (b) a nucleic acid which on the basis of the genetic code is degenerate to the DNA sequences defined in (a);
with the proviso that the nucleic acid molecule does not include the nucleic acid sequence of the ARO7 gene from *Saccharomyces cerevisiae*.

2. The isolated nucleic acid molecule according to claim 1, wherein said nucleic acid molecule is a desoxyribonucleic acid molecule.

3. The isolated nucleic acid molecule according to claim 1, further comprising a promoter suitable to control expression of the polypeptide encoded by said isolated nucleic acid, wherein the nucleic acid coding for a polypeptide with chorismate mutase activity is under the control of the promoter.

4. The isolated nucleic acid molecule according to claim 3, characterised in that the promoter is the MOX promoter or the FMD promoter from *Hansenula polymorpha*.

5. The isolated nucleic acid molecule according to claim 3, further comprising a heterologous nucleic acid sequence suitable to direct expression and optionally secretion of the polypeptide encoded by said isolated nucleic acid.

6. The isolated nucleic acid molecule according to claim 3, wherein the nucleic acid molecule contains at least a part of a vector, further wherein the vector is selected from: bacteriophages, plasmids, adenoviruses, vaccinia viruses, baculoviruses, SV40 virus and retroviruses.

7. The isolated nucleic acid molecule according to claim 3, wherein the nucleic acid further comprises a His-tag coding nucleic acid sequence and the expression of the nucleic acid molecule leads to the formation of a fusion protein with a His-tag.

8. A process for the production of a polypeptide with chorismate mutase activity, wherein the nucleic acid molecule according to claim 1 is expressed in a host cell suitable for the expression of a polypeptide encoded by said nucleic acid molecule and the protein is isolated if necessary.

9. The process according to claim 8 wherein the polypeptide with chorismate mutase activity produced is chemically modified or is post-translationally modified within said host cell.

10. A recombinant host cell, comprising the nucleic acid molecule according to claim 3, wherein the host cell is a prokaryotic or eukaryotic cell suitable for the expression of a polypeptide encoded by the nucleic acid molecule.

11. A process for the production of a polypeptide with chorismate mutase activity, wherein said polypeptide is expressed in a host cell according to claim 10.

12. The host cell according to claim 10 wherein the prokaryotic cell is selected from the group consisting of an *E. coli* cell and a *Bacillus subtilis* cell.

13. The recombinant host cell according to claim 10, wherein the eukaryotic cell is selected from the group consisting of a yeast cell, an insect cell, and a mammalian cell.

14. The non-naturally occurring host cell of claim 13, wherein the yeast cell is selected from the group consisting of a *Hansenula polymorpha* cell and a *Saccharomyces cerevisiae* cell.

15. The non-naturally occurring host cell of claim 13, wherein the mammalian cell is selected from the group consisting of a CHO cell, a COS cell and a HeLa cell.

* * * * *